(12) United States Patent
Akins et al.

(10) Patent No.: US 9,439,594 B2
(45) Date of Patent: Sep. 13, 2016

(54) WORK CAPACITIES TESTING APPARATUS AND METHOD

(71) Applicants: Robert Akins, Tucson, AZ (US); John Banks, Tucson, AZ (US); Mark Means, Tucson, AZ (US)

(72) Inventors: Robert Akins, Tucson, AZ (US); John Banks, Tucson, AZ (US); Mark Means, Tucson, AZ (US)

(*) Notice: Subject to any disclaimer, the term of this patent is extended or adjusted under 35 U.S.C. 154(b) by 0 days.

(21) Appl. No.: 14/307,393

(22) Filed: Jun. 17, 2014

(65) Prior Publication Data

US 2014/0295391 A1    Oct. 2, 2014

Related U.S. Application Data

(60) Division of application No. 13/658,729, filed on Oct. 23, 2012, now Pat. No. 8,752,428, which is a division of application No. 13/338,151, filed on Dec. 27, 2011, now Pat. No. 8,291,762, which is a continuation of application No. 10/586,436, filed on Jan. 31, 2008, now Pat. No. 8,082,786.

(51) Int. Cl.
| | |
|---|---|
| A61B 1/24 | (2006.01) |
| A61B 5/22 | (2006.01) |
| G09B 19/00 | (2006.01) |
| A61B 5/00 | (2006.01) |

(52) U.S. Cl.
CPC ............. *A61B 5/224* (2013.01); *A61B 5/225* (2013.01); *A61B 5/4824* (2013.01); *G09B 19/003* (2013.01); *A61B 2503/24* (2013.01)

(58) Field of Classification Search
USPC .............................................. 73/379.02, 788
See application file for complete search history.

(56) References Cited

U.S. PATENT DOCUMENTS

| | | |
|---|---|---|
| 3,788,062 A | 1/1974 | Booth |
| 3,861,201 A | 1/1975 | Kaindl |
| 4,662,227 A | 5/1987 | Peterson |
| 4,830,365 A | 5/1989 | March |
| 4,846,466 A | 7/1989 | Stima, III |
| 4,882,677 A | 11/1989 | Curran |
| 4,884,445 A | 12/1989 | Sadoff et al. |
| 4,884,454 A | 12/1989 | Johnson |
| 5,005,830 A | 4/1991 | Jones |

(Continued)

FOREIGN PATENT DOCUMENTS

GB        2153540 A    8/1985

OTHER PUBLICATIONS

057224230—European Supplementary Search Report dated May 6, 2009.

(Continued)

*Primary Examiner* — Jewel V Thompson
(74) *Attorney, Agent, or Firm* — Dale F. Regelman; Quarles & Brady LLP

(57) ABSTRACT

A portable work capacities testing apparatus comprising a portable computer, a hub releaseably interconnected with the portable computer, a dynamic strength and lifting device releaseably interconnected with the hub, a hand grip strength device releaseably interconnected with the hub, a finger pinch strength device releaseably interconnected with the hub, a forearm/wrist strength device releaseably interconnected with the hub, a handling/proprioception device releaseably interconnected with the hub, a finger flexion device releaseably interconnected with the hub, a whole body coordination device releaseably interconnected with the hub, and a strength push/pull/lift device releaseably interconnected with the hub.

4 Claims, 29 Drawing Sheets

(56) References Cited

U.S. PATENT DOCUMENTS

| | | |
|---|---|---|
| 5,038,769 A | 8/1991 | Krauser |
| 5,082,001 A | 1/1992 | Vanner |
| 5,112,286 A | 5/1992 | Jones |
| 5,142,910 A | 9/1992 | Litchman |
| 5,163,443 A | 11/1992 | Fry-Welch et al. |
| 5,275,045 A | 1/1994 | Johnson et al. |
| 5,369,365 A | 11/1994 | Waitman |
| 5,374,808 A | 12/1994 | Coultrip et al. |
| 5,396,253 A | 3/1995 | Chia |
| 5,577,848 A | 11/1996 | Bowen |
| RE35,598 E | 9/1997 | Sadoff et al. |
| 5,662,591 A | 9/1997 | Peindl et al. |
| 5,676,627 A | 10/1997 | Howse |
| 5,698,782 A | 12/1997 | Cledhill |
| 5,792,961 A | 8/1998 | Giebner et al. |
| 5,800,310 A | 9/1998 | Jones |
| 5,809,400 A | 9/1998 | Abramsky et al. |
| 5,848,594 A | 12/1998 | Matheson |
| 5,907,798 A | 5/1999 | Abramsky et al. |
| 5,909,645 A | 6/1999 | Abramsky et al. |
| 6,007,459 A | 12/1999 | Burgess |
| 6,041,660 A | 3/2000 | Fujitaka et al. |
| 6,186,961 B1 | 2/2001 | Hanoun |
| 6,227,047 B1 | 5/2001 | Livingston |
| 6,228,000 B1 | 5/2001 | Jones |
| 6,325,767 B1 | 12/2001 | Wolff et al. |
| 6,336,900 B1 | 1/2002 | Alleckson et al. |
| 6,353,533 B1 | 3/2002 | Ganthier et al. |
| 6,371,931 B1 | 4/2002 | Guillen |
| 6,494,103 B1 | 12/2002 | Loong |
| 6,544,172 B2 | 4/2003 | Toeppen-Sprigg |
| 6,678,549 B2 * | 1/2004 | Cusimano ............ A61B 5/4041 600/546 |
| 6,738,051 B2 | 5/2004 | Boyd et al. |
| 6,935,196 B1 | 8/2005 | Tumlin |
| 7,127,944 B1 | 10/2006 | Rozmaryn |
| 7,412,904 B2 * | 8/2008 | Holder ................ A61B 5/224 73/861.42 |
| 7,642,479 B2 | 1/2010 | Lin et al. |
| 8,228,307 B2 | 7/2012 | Lo |
| 8,339,373 B2 | 12/2012 | Chang |
| 8,350,830 B2 | 1/2013 | Hosoi et al. |
| 8,368,663 B2 | 2/2013 | Izadi et al. |
| 2002/0073931 A1 | 6/2002 | Boesch et al. |
| 2003/0135129 A1 | 7/2003 | Cusimano et al. |
| 2005/0092083 A1 | 5/2005 | Baratz et al. |
| 2006/0063647 A1 * | 3/2006 | Jones-Glaser ..... A63B 21/0085 482/49 |
| 2007/0032750 A1 | 2/2007 | Oster |
| 2007/0197938 A1 | 8/2007 | Tyson et al. |
| 2007/0231576 A1 | 10/2007 | Davis |
| 2008/0216570 A1 | 9/2008 | Andres et al. |
| 2008/0291158 A1 | 11/2008 | Park et al. |

OTHER PUBLICATIONS

2005206891—Australian Office Action dated Nov. 17, 2009.
057224230—European Office Action dated Jul. 3, 2011.
2553799—Canadian Office Action dated Mar. 20, 2013.
Boadella, et al., "Reliability of Upper Extremity Tests Measured by the Ergos Work Simulator: A Pilot Study," Journal of Occupational Rehabilitation, Dec. 2003, pp. 219-232, vol. 13, No. 4, Plenum Publishing Corporation.
European Office Action as mailed on Mar. 19, 2015 for European Patent Application No. 057224230.
Canadian Office Action as mailed on Sep. 11, 2014 for Canadian Patent Application No. 2,553,799.

* cited by examiner

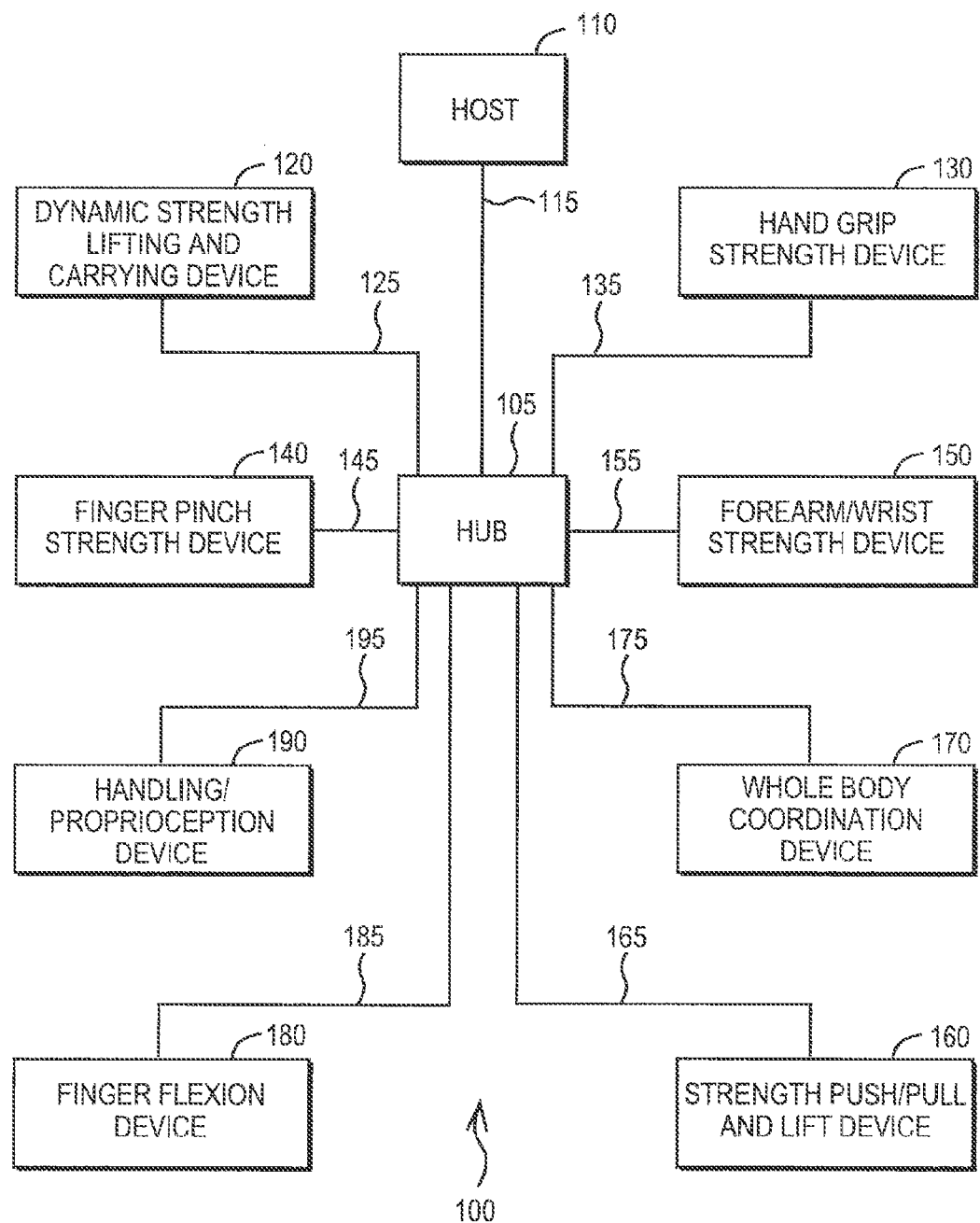

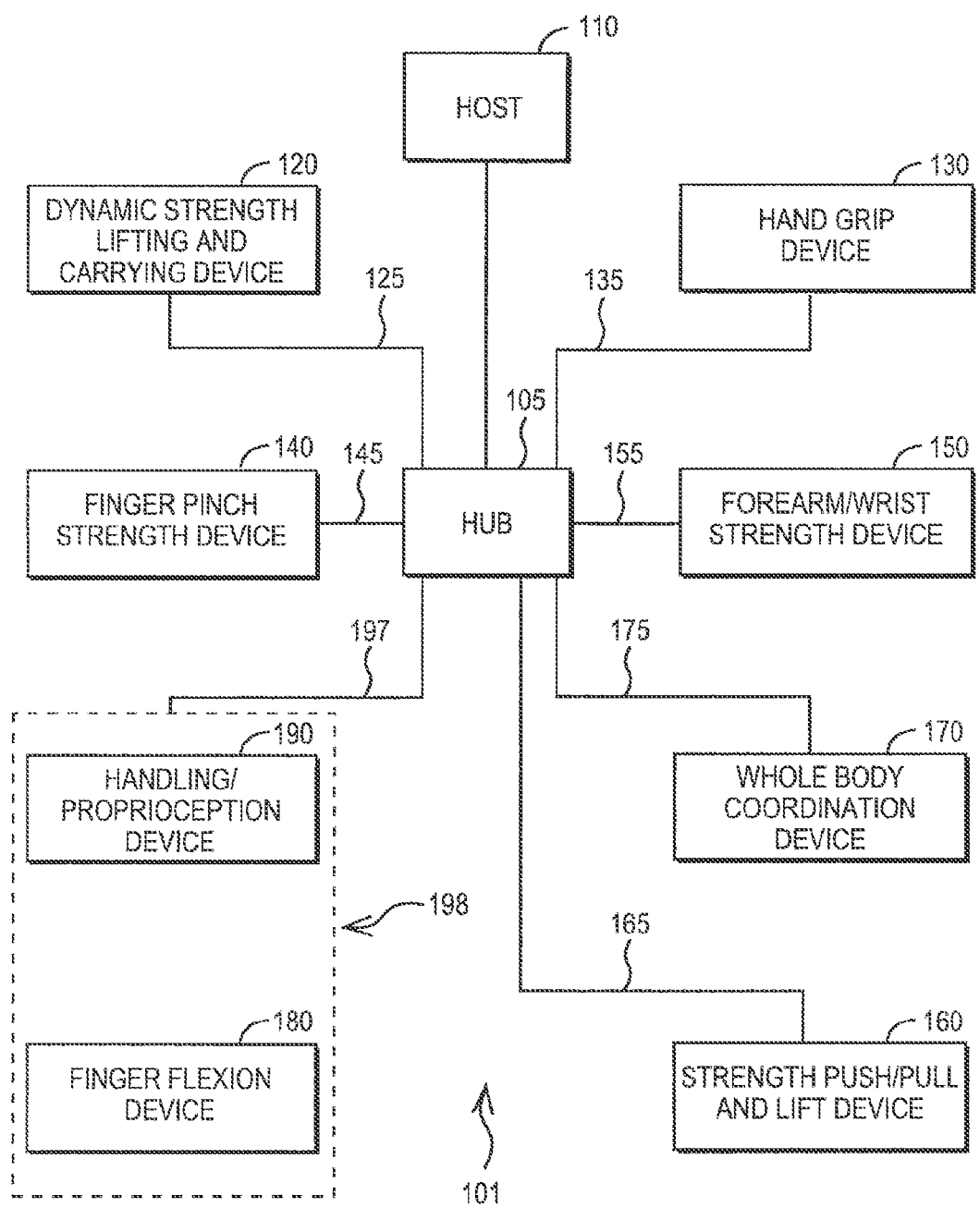

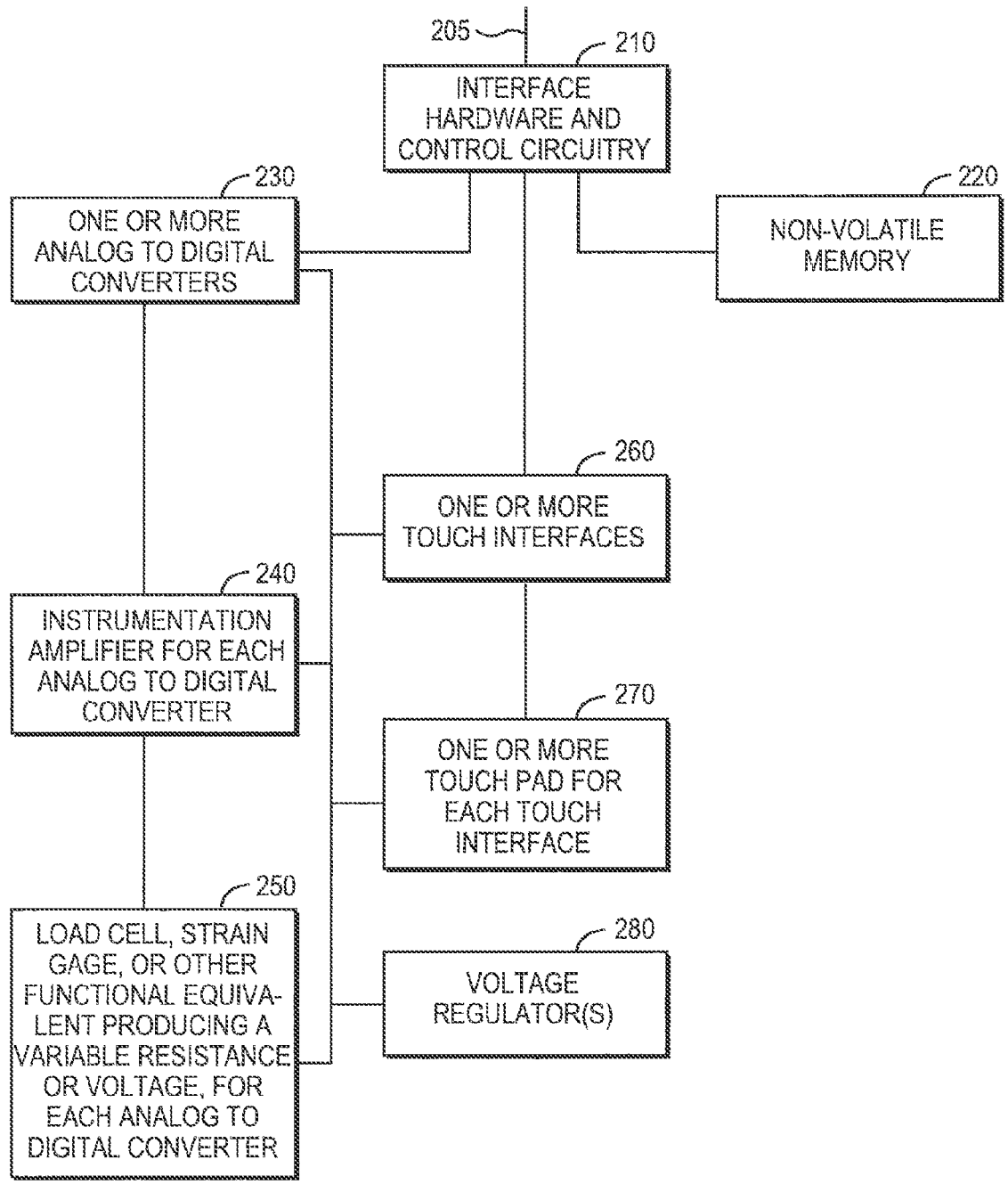

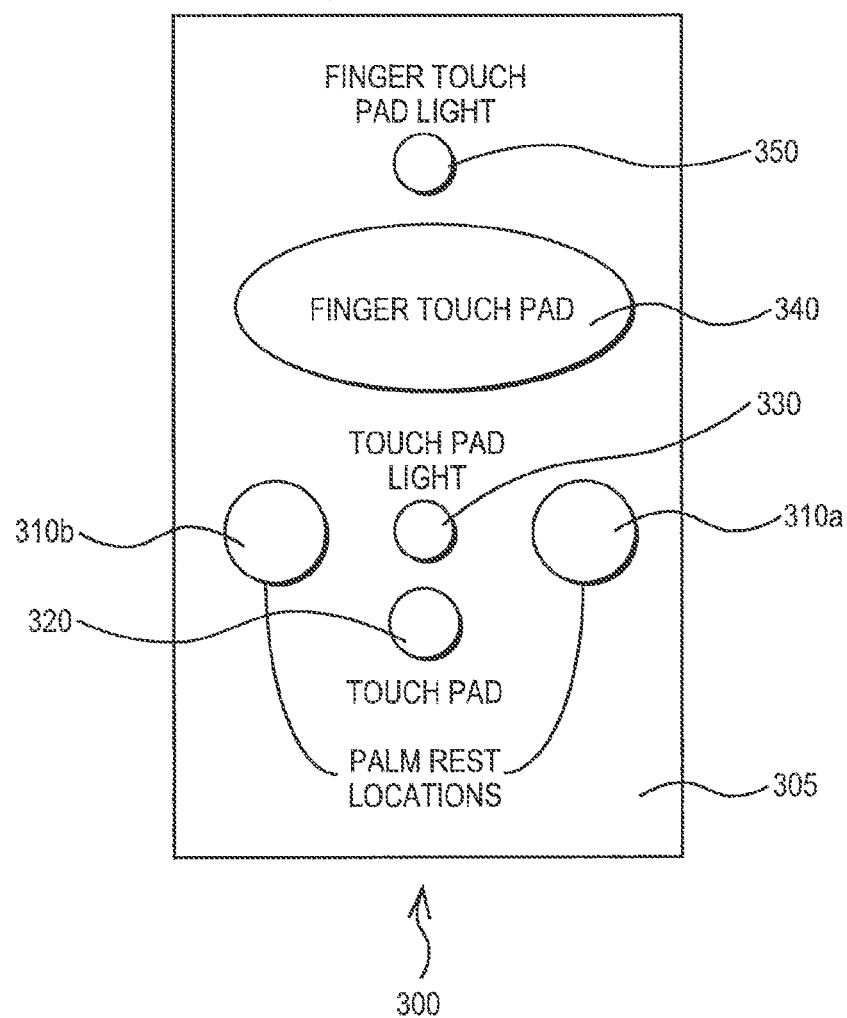

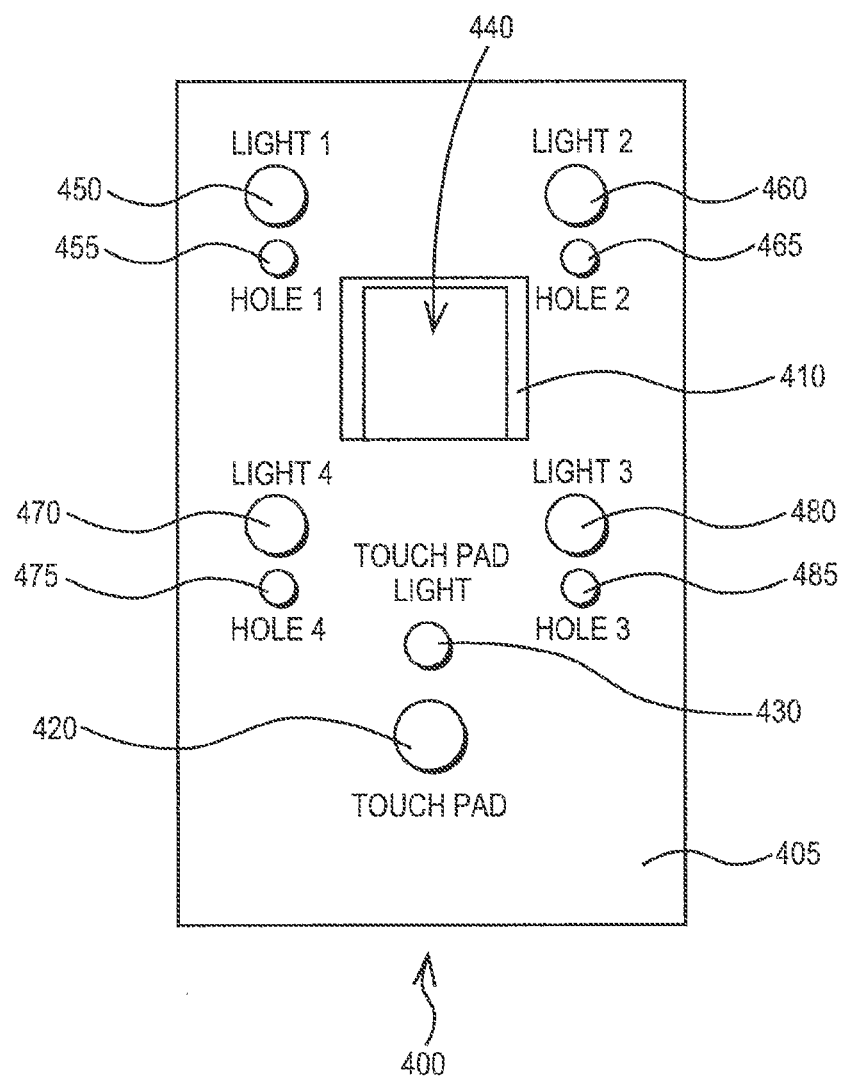

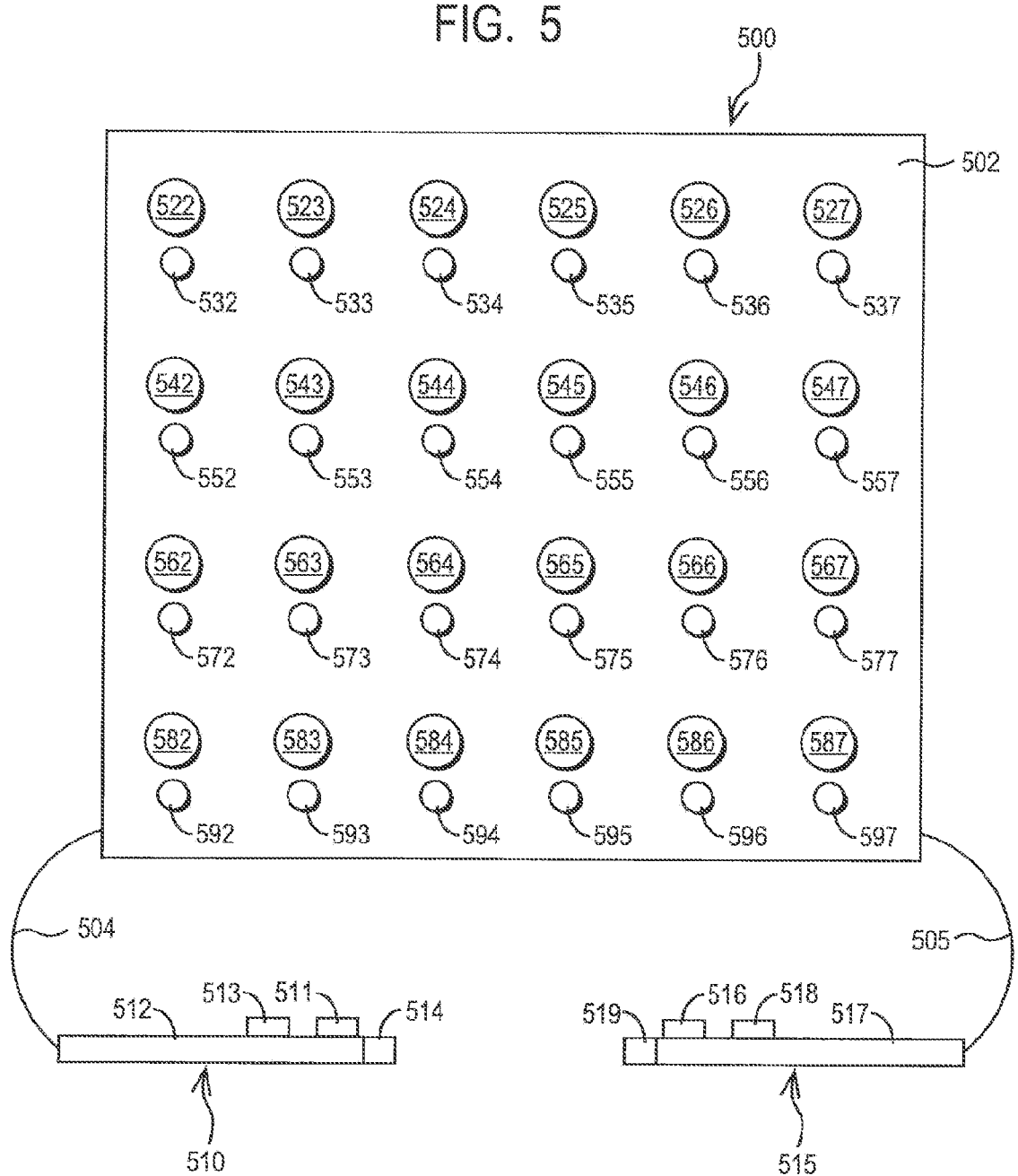

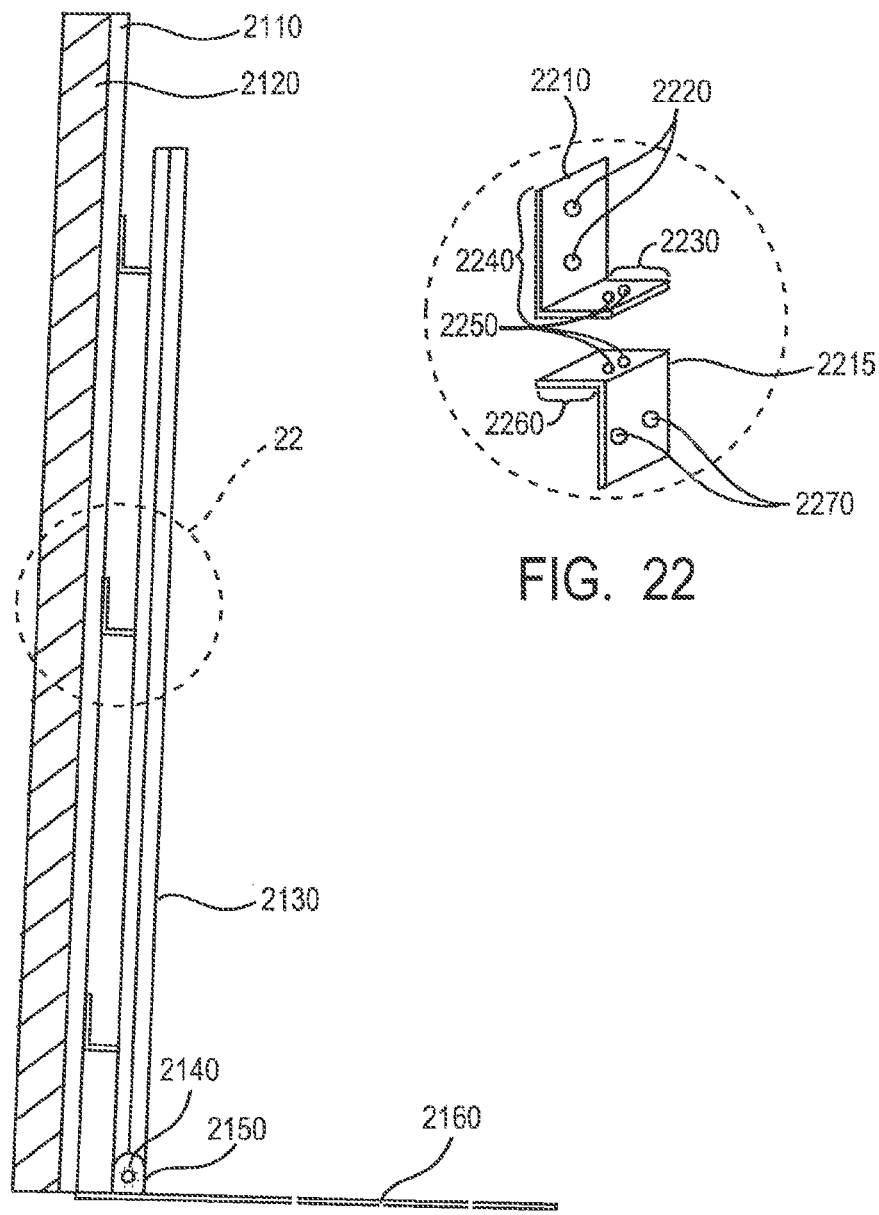

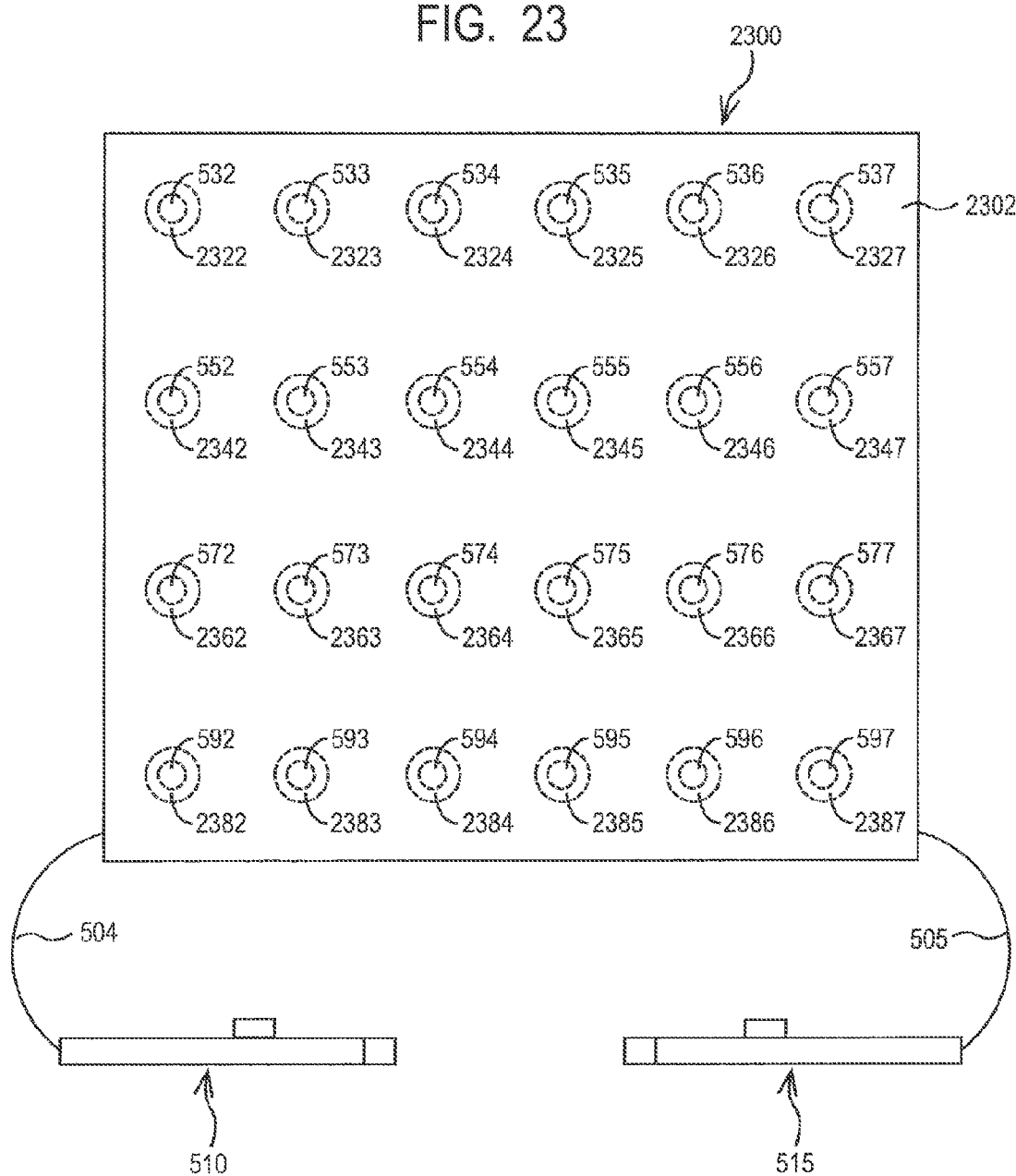

_US 9,439,594 B2_

WORK CAPACITIES TESTING APPARATUS AND METHOD

CROSS-REFERENCE TO RELATED APPLICATIONS

This application is a Divisional application claiming priority from a United States Divisional application having Ser. No. 13/658,729 filed Oct. 23, 2012, which claims priority from a United States Continuation application having Ser. No. 13/338,151 filed Dec. 27, 2011, now U.S. Pat. No. 8,291,762 which claims priority from a U.S. Utility application Ser. No. 10/586,436 filed Jan. 31, 2008, now U.S. Pat. No. 8,082,786, and which are incorporated by reference herein.

FIELD OF THE INVENTION

The invention relates to a work capacities testing apparatus, and a method using that apparatus.

BACKGROUND OF THE INVENTION

Work capacities testing systems currently available in the market place provide various forms of physical demand evaluations documenting safe work performance. These systems adhere to accepted standards and guidelines of work performance defined by the U.S. Dept. of Labor, NIOSH, ANSI, The MTM Association for Standards and Research ("MTM"), and others. In general these systems can measure physical performance such as strength, work posture and worker/work interface. Prior art systems are physically large, or are a collection of individual bulky test devices, occupying approximately 160 square feet, of floor space, or more. Some systems weigh as much as 1100 lbs. Prior work test devices each typically comprises dedicated components. Data is transferred from the device to the host for processing. Because each testing device is segregated from each of the other testing devices, the system is not portable. What is needed is a portable work capacities testing apparatus, and a method using that portable apparatus.

SUMMARY OF THE INVENTION

Applicants' invention includes a portable work capacities testing apparatus, and a method using that portable apparatus. Applicants' apparatus comprises a portable computer, a hub releaseably interconnected with the portable computer, a dynamic strength and lifting device releaseably interconnected with the hub, a hand grip strength device releaseably interconnected with the hub, a finger pinch strength device releaseably interconnected with the hub, a forearm/wrist strength device releaseably interconnected with the hub, a handling/proprioception device releaseably interconnected with the hub, a finger flexion device releaseably interconnected with the hub, a whole body coordination device releaseably interconnected with the hub, and a strength push/pull/lift device releaseably interconnected with the hub.

BRIEF DESCRIPTIONS OF THE FIGURES

The invention will be better understood from a reading of the following detailed description taken in conjunction with the drawings in which like reference designators are used to designate like elements, and in which:

FIG. 1A is a block diagram showing a first embodiment of Applicants' apparatus;

FIG. 1B is a block diagram showing a second embodiment of Applicants' apparatus;

FIG. 2 is a block diagram showing Applicants' integrated testing device;

FIG. 3 is a perspective view of Applicants' Finger Flexion Station;

FIG. 4 is a perspective view of Applicants' Handling/Proprioception Station;

FIG. 5 is a front view of a first embodiment of Applicants' Whole Body Coordination Station;

FIG. 21 is a side view of Applicants' monopole support device;

FIG. 22 is a perspective view of the fasteners used to affix the monopole support device of FIG. 21 to a wall;

FIG. 23 is a front view of a second embodiment of Applicants' Whole Body Coordination Station;

DETAILED DESCRIPTION OF THE PREFERRED EMBODIMENTS

Figure 6A:
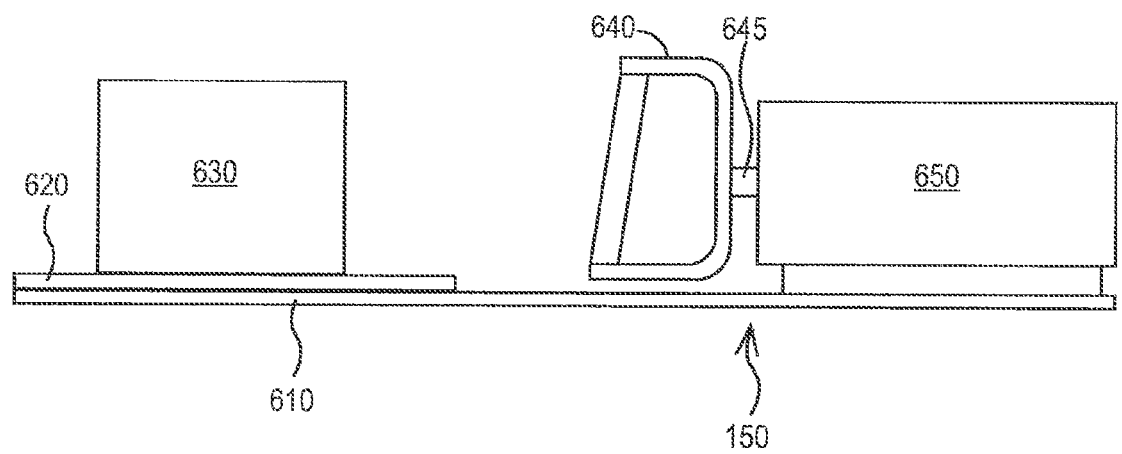
FIG. 6A is a perspective view of a first embodiment of Applicants' Forearm/Wrist Strength Device.

This invention is described in preferred embodiments in the following description with reference to the Figures, in which like numbers represent the same or similar elements. Applicants' invention includes a work capacities testing apparatus and method which can perform the currently used testing protocols using a portable apparatus which includes a plurality of integrated testing devices. Using Applicants' apparatus and method, work capacity testing can be performed at a place of employment, or at a remote location, while requiring less than 20 square feet of floor space and weighing approximately 240 pounds excluding test weights. Up to 110 pounds of test weights can be shipped depending on the test circumstances.

A communication network permits bidirectional communication between a portable computer and a plurality of test devices. In certain embodiments, the computer monitors tasks by polling four multiple static strength test devices, three performance test devices, and one dynamic test device. In certain embodiments, one or more test devices interconnect with the computer through a communication hub. In other embodiments, one or more integrated test devices interconnect with the computer directly.

Referring now to FIG. 1A, shows embodiment 100 of Applicants' apparatus. In the illustrated embodiment of FIG. 1A, Applicants' work testing system 100 includes host computer 110; a dynamic test device 120; four multiple static strength test devices 130, 140, 150, and 160; three performance test devices 170, 180, and 190; a communication hub 105; and communication links 115, 125, 135, 145, 155, 165, 175, 185, and 195. In certain embodiments, communication links 115, 125, 135, 145, 155, 165, 175, 185, and 195, are each selected from the group which includes a Universal Serial Bus ("USB") interconnection, a Fire Wire interconnection, an IEEE-1394 interconnection, or wireless connection such as Bluetooth, WiFi, and Wireless USB, and the like.

In certain embodiments, host computer 110 comprises a portable computer. Such a portable computer is often referred to as a "lap top" or a "handheld" computer. In these embodiments, host computer 110 is physically collocated with the other elements of Applicants' work capacities testing apparatus. In other embodiments, host computer 110 is remotely located from the other elements of Applicants' work capacities testing apparatus. In these embodiments, communication link 115 comprises a local area network, a wide area network, the Internet, and combinations thereof. In these remote computer embodiments, host computer 110 comprises a computer system, such as a mainframe, personal computer, workstation, and combinations thereof, including an operating system such as Windows, AIX, Unix, MVS, LINUX, etc. (Windows is a registered trademark of Microsoft Corporation; AIX is a registered trademark and MVS is a trademark of IBM Corporation; and UNIX is a registered trademark in the United States and other countries licensed exclusively through The Open Group.)

FIG. 1B shows embodiment 101 of Applicants' apparatus. In the illustrated embodiment of FIG. 1B, devices 180 and 190 are integrated into a single device 198. Communication link 197 releaseably interconnects device 198 and hub 105. Communication link 197 is selected from the group which includes a Universal Serial Bus ("USB") interconnection, a Fire Wire interconnection, an IEEE-1394 interconnection, or wireless connection such as Bluetooth, WiFi, and Wireless USB, and the like.

In the illustrated embodiments of FIGS. 1A and 1B, Dynamic Strength Lifting and Carrying Device 120 is releaseably interconnected with hub 105 via communication link 125, Hand Grip Strength Device 130 is releaseably interconnected with hub 105 via communication link 135, Finger Pinch Strength Device 140 is releaseably interconnected with hub 105 via communication link 145, Forearm/Wrist Strength Device 150 is releaseably interconnected with hub 105 via communication link 155, Strength Push/Pull/Lift Device 160 is releaseably interconnected with hub 105 via communication link 165, Whole Body Coordination Device 170 is releaseably interconnected with hub 105 via communication link 175, Finger Flexion Device 180 is releaseably interconnected with hub 105 via communication link 185, and Handling/Proprioception Device 190 is releaseably interconnected with hub 105 via communication link 195. By "releaseably interconnected," Applicants mean the interconnection can be alternatingly established and terminated using only a person's hands with no tools are required.

In certain embodiments where the host provides sufficient USB ports for the devices in use, an external hub 105 is unnecessary.

In certain embodiments of Applicants' apparatus and method, one or more of test devices 120, 130, 140, 150, 160, 170, 180, and/or 190, comprise integrated devices. By "integrated device," Applicants mean a testing device which comprises a processor, instructions used by the processor to implement one or more test protocols, and a data acquisition system to locally store the results of the tests performed. Using an integrated device, the interconnected host computer need not comprise software/firmware designed to operate the interconnected integrated device.

A "non-integrated device" does not comprise a processor, in combination with instructions used by the processor to implement one or more test protocols, in combination with a data acquisition system to locally store the results of the tests performed. Non-integrated devices are controlled by an interconnected host computer comprising software/firmware designed to operate that interconnected, non-integrated device.

In certain embodiments of Applicants' invention, each of devices 120, 130, 140, 150, 160, 170, 180, and/or 190, comprise an integrated device, as defined herein. In other embodiments, Applicants' systems 100 and/or 101 comprises one or more integrated devices and one or more non-integrated devices, wherein one or more of those one or more non-integrated devices comprise a data acquisition system and a USB interface.

As a general matter, each of Applicants' integrated testing devices measures force applied to a surface. Applicants' apparatus and method then convert that measured force to an analog electrical signal, and then converts that analog signal to a digital value corresponding to the force applied. This conversion to a digital value is done at close proximity to the load cell or strain gage in order to minimize or eliminate environmental factors, such as temperature and induced electrical interference, from affecting the measurement. By "close proximity," Applicants mean within about 5 centimeters. In certain embodiments, the conversion from a measured force to an analog signal, and the conversion of that analog signal to a digital signal is performed with an electrically and RF shielded environment.

The computed digital value is then transferred to the host. In certain embodiments, the conversion of the raw digital value to pounds, kilograms or any other unit of measure is performed by the host. In other embodiments, the conversion of the raw digital value to pounds, kilograms or any other unit of measure is performed by the integrated testing device itself.

In certain embodiments, each integrated testing device is assigned a unique identifier which can be read by a host. Use of this unique identifier allows a host to distinguish one testing device from other devices in Applicants' system. Further, use of these unique identifiers permits the host to individually address each individual device comprising Applicants' system.

FIG. 2 shows a block diagram of Applicants' integrated test device. Applicants' integrated testing device includes a local controller 210 which comprises one or more Interface Circuits which facilitate communication with the host, a Non-Volatile Memory Device 220 for data storage, Analog to Digital Converter 230 which converts analog force data to digital data, and Load Cell or Strain Gage 250 and optional voltage regulator(s) for power management 280. The information stored in the non-volatile memory includes the device identifier, and/or particular calibration data for that testing device, and/or other information needed to operate the device. Such calibration data is used by control circuitry 210 and/or the host computer to convert the output of an Analog to Digital Controller force data in pounds or kilograms or other units of measure.

Control circuitry 210 receives and recognizes a start command from the host instructing the test device to begin converting analog data to digital data, and to manage the transmission of data to the host. The host can also simply read data stored in the output register of the Analog to Digital Converter. Control circuitry 210 also receives and recognizes commands to stop transmitting data, reset its operation, power up or down, and store new calibration or other data.

In certain embodiments, Interface Hardware/Control Circuitry 210 includes a Cypress EZ-USB circuit which includes circuitry 1400. In certain embodiments, Analog to Digital Converter 230 comprises a Analog Devices AD7715 which includes an embedded instrumentation amplifier 240. In certain embodiments, Load Cell/Strain Gage 250 comprises an Interface SM250 circuit. In certain embodiments, Non-Volatile Memory 220 comprises Microchip Technology 24AA128ST or equivalent. In certain embodiments, Voltage Regulator 280 comprises a National Semiconductor LP2992AIM5-3.3 or equivalent. One of ordinary skill in the art will appreciate, that the above identified preferred circuits or devices can be replaced by other components.

Applicants' integrated testing devices include elements 210 and 220. Certain of Applicants' integrated devices further include element 230 and/or element 240 and/or element 250 and/or element 260 and/or element 270 and/or element 280.

In addition to the above features, Applicants' integrated test devices optionally include circuitry to monitor several discrete sensors and operate lights, LEDs or mechanical actuators. In certain embodiments, Applicants' integrated devices include additional Operation Amplifier(s), Analog to Digital Converter(s), Load Cell(s) or Strain Gage(s).

Applicants' static strength integrated testing devices include Finger Pinch Strength Device 140, Hand Grip Strength Device 130, Forearm/Wrist Strength Device 150, and a Strength Push/Pull/Lift Device 160. In certain embodiments, Applicants' system 100 further includes additional devices to measure static strength of the finger, ankle, knee, shoulder, hip or other joints.

Applicants' static strength integrated testing devices measure force capacities in a static environment for various biomechanics of an individual. These integrated devices comprise one or more load cells or strain gages that convert a force applied to a surface into a resistance or an electrical signal. The electrical signal is converted to digital data which is force data. The data is sent to the host for analysis.

Figure 13:
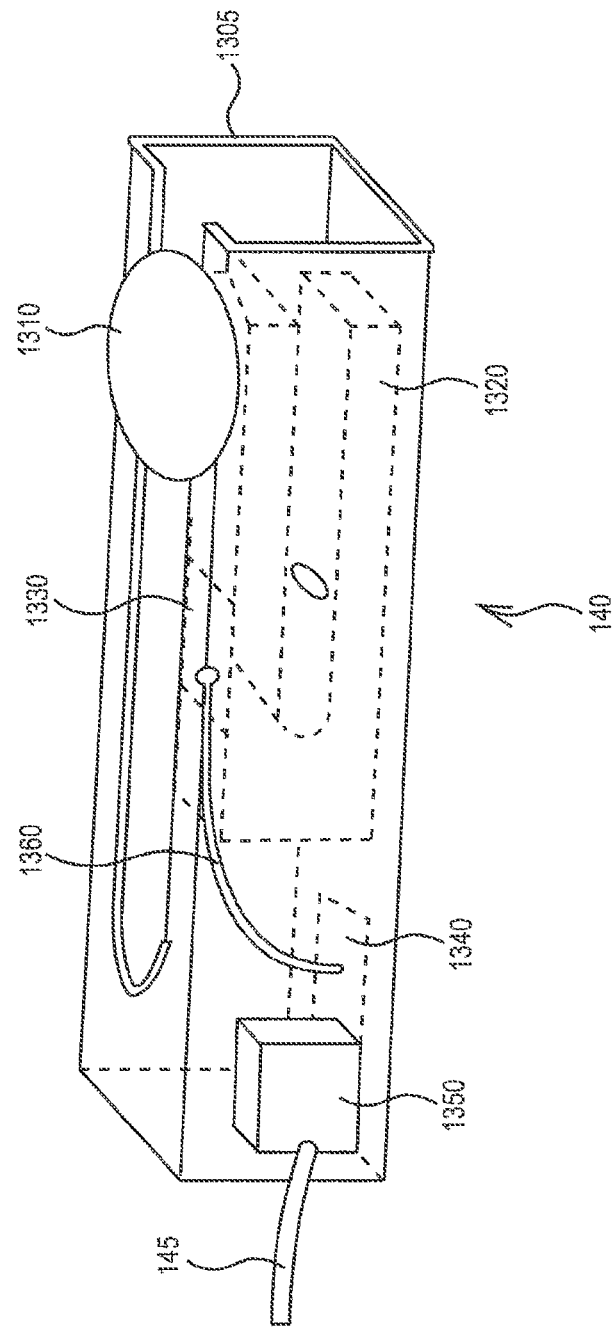
FIG. 13 is a perspective view of Applicants' Finger Pinch Strength Device.

Finger Pinch Strength Device 140 measures the finger pinching strength of an individual. The device comprises a load cell or strain gage, and operates in conjunction with the host computer to measure the pinch strength of an individual. Referring now to FIG. 13, Finger Pinch Strength Device 140 comprises housing 1305. In certain embodiments, housing 1305 is formed from one or more metallic materials, such as for example steel, aluminum, and the like. In certain embodiments, housing 1305 has an essentially square cross-section. In certain embodiments, the walls comprising housing 1305 are about 3-½ inches long, ¾ inch high and ¾ inch wide.

Device 140 further comprises depressable member 1310. In the illustrated embodiment of FIG. 13, depressable member 1310 is circular. In other embodiments, member 1310 has a square shape, a rectangular shape, a pentagonal shape, or a hexagonal shape.

In use, the subject grasps housing 1305 with his/her hand with the thumb disposed on the top surface of member 1310. Depressable member 1310 records the opposing action of the thumb pressing against the fingers of the test subject's hand. Member 1310 is attached to the top of load cell bended beam 1320. In certain embodiments, the distance of member 1310 from the bottom of housing 1305 is about one inch to analogize the subject's functional pinch capability to actual workplace performance requirements. In these embodiments, Applicants' Finger Pinch Strength Device 140 provides a comparison of the test subject's finger pinch action to real-world on-the-job activities. Applicants' device 140 differs from prior art devices which typically have a measurement surface disposed less than 0.75 inches from the bottom surface of the test device.

Figure 14:
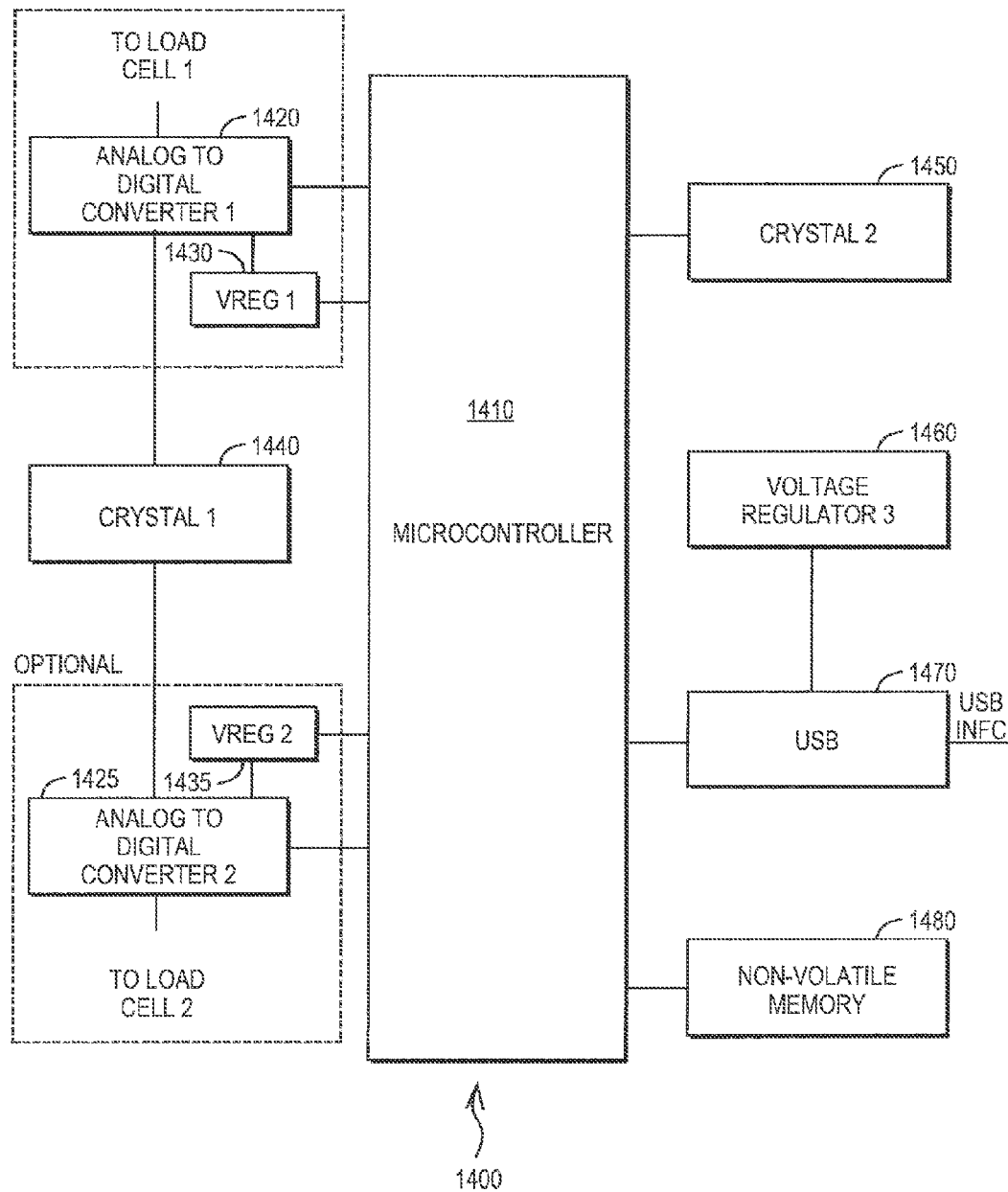
FIG. 14 is a block diagram showing the electrical components of Applicants' Finger Pinch, Hand Grip Strength Devices, Forearm/Wrist Strength Device, Dynamic Lifting and Carrying Device, and Strength Push/Pull/Lift Device.
Figure 15:
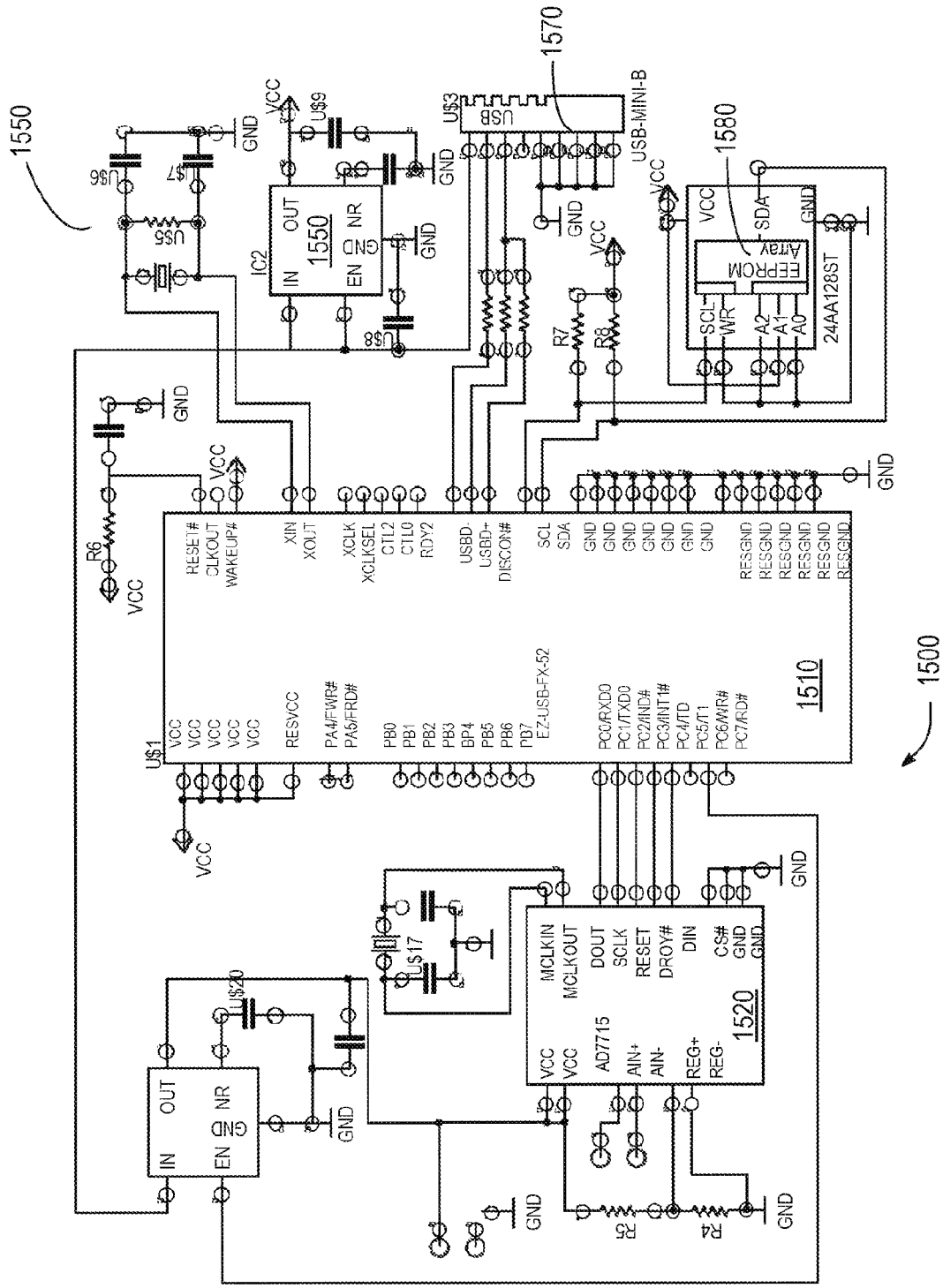
FIG. 15 is a circuit diagram showing circuitry to implement the components of FIG. 14.

Communication link 1360 interconnects load cell circuitry 1330 and integrated test device circuitry 1340. Communication link 145 (FIGS. 1A and 1B) interconnects circuitry 1340 to the host computer via cable connector 1350. In certain embodiments, circuitry 1340 comprises a part or all of the elements shown in FIG. 14. Referring to FIGS. 13 and 14, load cell bended beam 1320 is interconnected to analog to digital converter ("ADC") 1420 by communication link 1360. ADC 1420 is interconnected to voltage regulator 1430 and crystal 1440. Voltage regulator 1430 is interconnected to microcontroller 1410. Crystal 1450, USB interface 1470, and memory 1480, are interconnected to microcontroller 1410. Voltage regulator 1460 is interconnected to USB interface 1470. In certain embodiments, the elements shown in FIG. 14 are implemented using the circuitry shown in FIG. 15. The circuitry shown in FIGS. 14 and 15 can be used for all strength devices shown on FIGS. 1A and 1B. The FIGS. 1A and 1B devices Whole Body Coordination Device 170 and Handling/Proprioception 190 and Finger Flexion Device 180 may also use the circuitry shown in FIGS. 14 and 15 by using the all components on FIGS. 14 and 15 except for the Analog to Digital Converters 1420 and 1425 which are replaced by components 1710 or 1910 in FIG. 17 or 19 respectively.

USB interface 1470 provides a data path to the host. Other types of interfaces such as Ethernet, Wireless USB, Bluetooth, IEEE Specification 802.11 (the "IEEE Specification"), and the like, can be used depending upon the features of the MICROCONTROLLER chosen. As those skilled in the art will appreciate, the IEEE Specification comprises a family of specifications developed by the IEEE for wireless LAN technology.

The IEEE Specification specifies an over-the-air interface between a wireless client, such as for example projector 100, and a base station or between two wireless clients. The IEEE accepted the IEEE Specification in 1997. There are several specifications in the 802.11 family, including (i) specification 802.11 which applies to wireless LANs and provides 1 or 2 Mbps transmission in the 2.4 GHz band using either frequency hopping spread spectrum (FHSS) or direct sequence spread spectrum (DSSS); (ii) specification 802.11a which comprises an extension to 802.11 that applies to wireless LANs and provides up to 54 Mbps in the 5 GHz band using an orthogonal frequency division multiplexing encoding scheme rather than FHSS or DSSS; (iii) specification 802.11b, sometimes referred to as 802.11 High Rate or Wi-Fi, which comprises an extension to 802.11 that applies to wireless LANS and provides up to about 11 Mbps transmission in the 2.4 GHz band; and/or (iv) specification 802.11g which applies to wireless LANs and provides 20+ Mbps in the 2.4 GHz band; and/or (v) other specifications in the 802.11 family.

Voltage regulator 1460 provides voltage regulation which microcontroller 1410 may optionally monitor. Crystal 1440 and crystal 1450 provide timing for microcontroller 1410 and ADC 1420 respectively. Microcontroller 1410 coordinates data transfer and handshaking signals between the USB interface 1470, ADC 1420, and non-volatile memory 1480. ADC 1420 provides amplification of the load cell signal, filtering, conversion from analog to digital, and calibration functions for and as directed by microcontroller 1410. The voltage regulator 1430 and optional voltage regulator 1435 are used to provide power to the associated circuitry and remove power from the associated circuitry to conserver power. The optional voltage regulator 1435 and ADC 1425 and interface to Load Cell 2 are used by the Forearm/Wrist Strength Device and Strength Push/Pull/Lift Device which require two load cells. In addition other devices requiring dual load cells, such as a dual grip strength device or a dual pinch strength device measures simultaneous strength.

Figure 16:
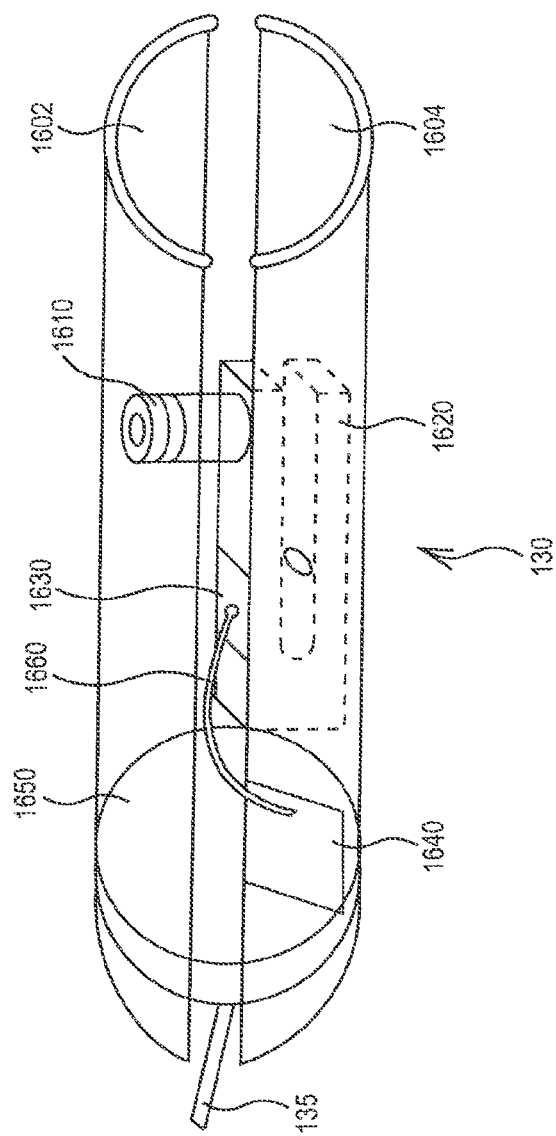
FIG. 16 is a perspective view of Applicants' Hand Grip Strength Device.

Hand Grip Strength Device 130 measures hand gripping strength of an individual. The device comprises a load cell or strain gage, and operates in conjunction with the host computer to measure the grip strength of an individual. Referring now to FIG. 16, Hand Grip Strength Device 130 comprises upper housing portion 1602 and lower housing portion 1604. In certain embodiments, housing portions 1602 and 1604 comprise one or more metallic materials, such as steel, aluminum, and the like. In certain embodiments, Hand Grip Strength Device 130 is about 4.5 inches long and about 1.5 inches in diameter. As those skilled in the art will appreciate, the length and/or diameter of device 130 can be adjusted to fit the hand grasp and circumstances of the subject being tested.

Pivot ring 1650 joins upper housing portion 1602 and lower housing portion 1604, and functions as a free floating pivot point. Member 1610 interconnects upper housing portion 1602 and the top surface of load cell bended beam 1620. As the test subject squeezes upper housing portion 1602 and lower housing portion 1604 together, member 1610 transfers mechanical energy to load cell bended beam 1620.

Communication link 1660 interconnects load cell circuitry 1630 and integrated test device circuitry 1640. Communication link 135 (FIG. 1A and FIG. 1B) interconnects circuitry 1640 to the host computer. In certain embodiments, integrated test device circuitry 1640 comprises a part or all of the elements shown in FIG. 14. Load cell circuitry 1630 is interconnected to analog to digital converter ("ADC") 1420 (FIG. 14) by communication link 1640. ADC 1420 is interconnected to voltage regulator 1430 (FIG. 14) and crystal 1440 (FIG. 14). Voltage regulator 1430 (FIG. 14) is interconnected to microcontroller 1410 (FIG. 14). Crystal 1450 (FIG. 14), USB interconnect 1470 (FIG. 14), and memory 1480 (FIG. 14), are interconnected to microcontroller 1410. Voltage regulator 1460 (FIG. 14) is interconnected to USB interconnect 1470. In certain embodiments, the elements shown in FIG. 14 are implemented using the circuitry shown in FIG. 15.

In other embodiments a dual channel device can be built using the optional 1425 and 1435 to support multiple grip and pinch load cells or other combinations. Someone skilled in the art can see that this can be extended to as many channels as needed by adding additional optional blocks.

Forearm/Wrist Strength Device 150 measures the strength of the forearm and the wrist in either the flexion/extension or pronation/supination axes. As those skilled in the art will appreciate, bending the wrist inwardly is referred to as flexion, bending the wrist outwardly is referred to as extension, rotating the wrist/forearm inwardly is referred to pronation, and rotating the wrist/forearm outwardly is referred to as supination. Applicants' Forearm/Wrist Strength Device comprises an integrated device which allows the above-recited tests to be performed using a single testing apparatus.

Applicants' Forearm/Wrist Strength Device comprises a multi-axis, isometric strength testing device using two load cells or strain gauges. Such integration allows a compact footprint and minimizes the number of discrete hardware components, thereby enhancing portability. In addition, Applicants' system accommodates differing extremes in physiology amongst tested persons. Using prior art devices and methods, individuals who are either small in stature, or very large in stature, cannot be tested using the available computerized testing devices. In marked contrast, however, Applicants' system is adjustable thereby allowing accurate testing regardless of the physical size of the person's forearm, hand or wrist.

FIG. 6A illustrates a first embodiment of Applicants' Forearm/Wrist Strength Device 150. Referring now to FIG. 6A, Applicants' Forearm/Wrist Strength Device 150 comprises a platform base 610 which is about 4" wide and about 14" long. Platform base 610 is formed from a rigid material, including metal, wood, plastic, and combinations thereof.

Shuttle 620 and sensing unit 650 are attached to the platform 610. Shuttle 620 is moveably disposed at a first end, i.e. the evaluee's end, of platform 610, and sensing unit 650 is disposed at the opposite end of platform 610. Shuttle portion can be moved closer or further away from the sensing unit handle 640 to accommodate the differences in hand/wrist and forearm size. Handle 640 contains a shaft 645 that can be removed from the sensing unit 650 and repositioned at about 30 degree angle increments for pronation and supination test activities. Immobilization device 630 is attached to shuttle assembly 620. In certain embodiments, device 630 comprises two semicircular halves that hingedly open to accommodate the evaluee's wrist. Immobilization device 630 is then closed around the evaluee's wrist. In certain embodiments, device 630 is maintained in the closed configuration using, for example, a flexible band comprising a plurality of hook and loop fasteners.

Figure 6B:
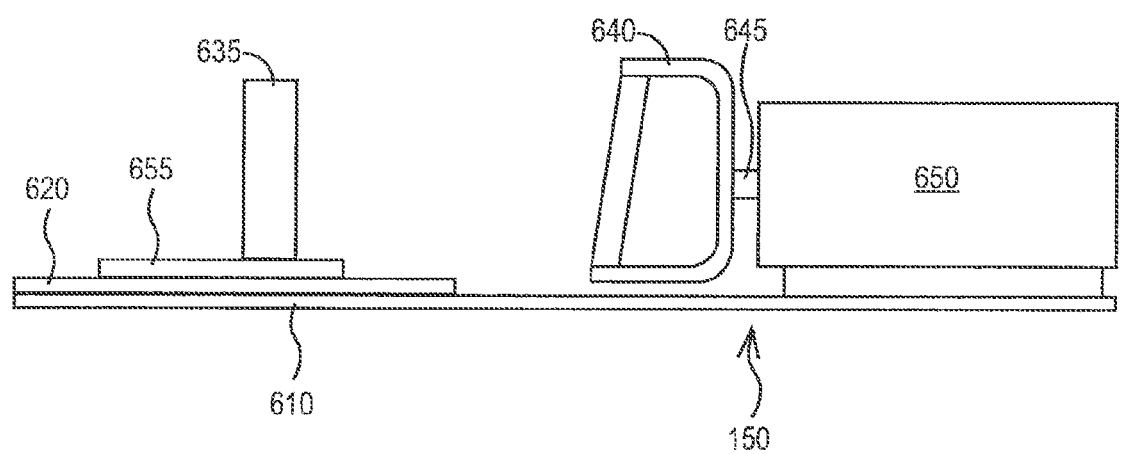
FIG. 6B is a perspective view of a second embodiment of Applicants' Forearm/Wrist Strength Device.
Figure 6C:
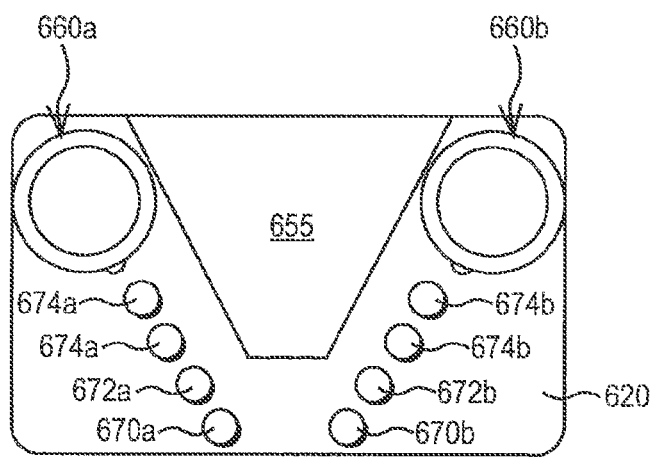
FIG. 6C is a top diagram view of a second embodiment of Applicants' Forearm/Wrist Strength Device.
Figure 6D:
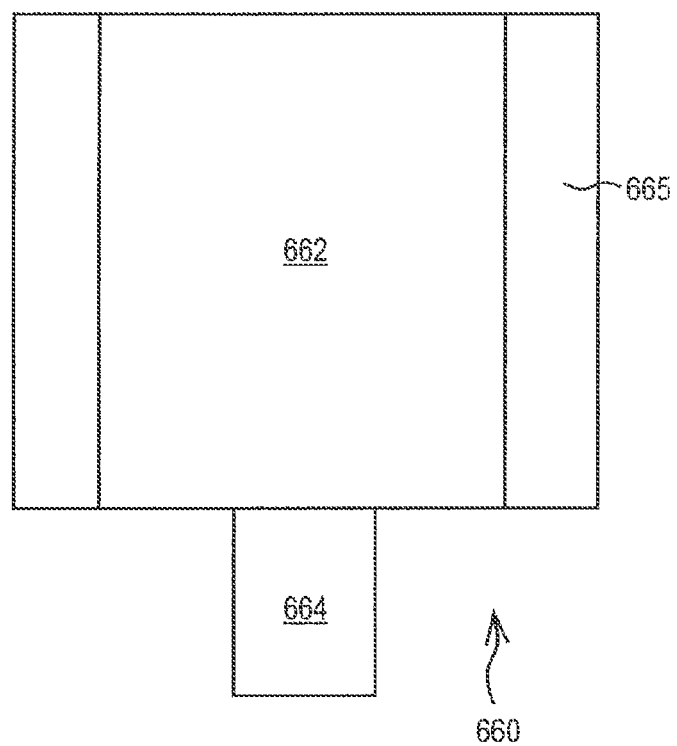
FIG. 6D is a cross-sectional view of Applicants' Forearm/Wrist Strength Device post assembly.

Referring now to FIGS. 6B, 6C, and 6D, in other embodiments the immobilization device consists of platform 610, shuttle 620 slidingly disposed on platform 610, cushion 655, and pair of moveable posts 660. Shuttle 620 is formed to include a plurality of aperture sets, such as aperture sets 670*a*/670*b*, 672*a*/672*b*, 674*a*/674*b* shown in FIG. 6C. Referring now to FIG. 6D, post assembly 660 comprises a cylindrical member 662 having a first diameter, a second cylindrical member 664 having a second diameter, wherein the second cylindrical member 664 is attached to the bottom portion of first cylindrical member 662 and extending outwardly therefrom, wherein the first diameter is greater than the second diameter. Member 664 is dimensioned such that member 664 can be removeably inserted into one or the aperture disposed in shuttle 620. First cylindrical member 662 and second cylindrical member are formed from one or more rigid materials, such as for example wood, metal, engineering plastic, ceramic, and the like.

Covering 665 is disposed around the vertical surface of first cylindrical member 662. Covering 665 is formed from one or more flexible materials, such as a polyethylene foam, a polyurethane foam, a polyvinyl foam, and the like.

Referring again to FIG. 6C, post assemblies 660a and 660b are removeably disposed in a set of apertures disposed in shuttle 620 to accommodate the evaluee's wrist size and circumstances. The top view on FIG. 6C shows the various sets of apertures that can be used to position post assemblies 660a and 660b to accommodate the evaluee's wrist size.

The Forearm/Wrist Strength Testing Device as shown in FIG. 6B uses an immobilization device to assure that the individual is aligned in the proper axis required for the test activity. The immobilization device consists of a moveable platform attached to the shuttle that has a cushion rest centered on the platform. Two moveable posts 635 having a cushioned cover are attached to the platform using a threaded stud on the bottom. The posts are positioned at accommodating widths on the platform by threading the stud into the platform. In other embodiments the posts can be positioned and affixed in place using a ball release pin, a compression stud or other connecting hardware.

Using either the embodiment of FIG. 6A or FIG. 6B, the person being tested grips the sensing unit handle 640 and, depending on the test, either rotates the handle 640 clockwise or counterclockwise, or moves shaft 645 laterally. The sensing unit 650 records the test movements by using two load cells measuring the respective test moves.

In certain embodiments, Applicants' Forearm/Wrist Strength Device 150 includes a third load cell or strain gage. Using these embodiments, Applicants' Forearm/Wrist Strength Device 150 can measure radial and lunar deviation strength, which is movement of the wrist in the up and down axis. In certain embodiments, Applicants' Forearm/Wrist Strength Device further includes a fourth strain gage or load cell thereby adding grip strength measurement capability to Applicants' device 150.

Applicants' Strength Push/Pull/Lift Device 160 is used to take whole body bilateral strength measurements with the whole body stationary. Device 160 works "bilaterally." By "bilateral measurement," Applicants mean device 160 measures the force applied by both sides of the body at the same time. For pushing, pulling or lifting there are two handles. Associated hardware includes positioning equipment to place the handles in the position required by the testing protocol being used.

The tested individual apples force to a stationary object, and device 160 measures push, pull, and/or lifting strength for both sides of the body at the same time. Device 160 includes two load cells or strain gages in combination one or two communication links Measuring sensors are disposed in the handles grasped by the tested individual. These load cells or strain gages sense the direction the individual is pushing, pulling or lifting. The position of the handles can be varied, i.e. vertical, or horizontal, or any position in between such that the individual being tested can be in any body position to push, pull or lift the handles.

Figure 8:
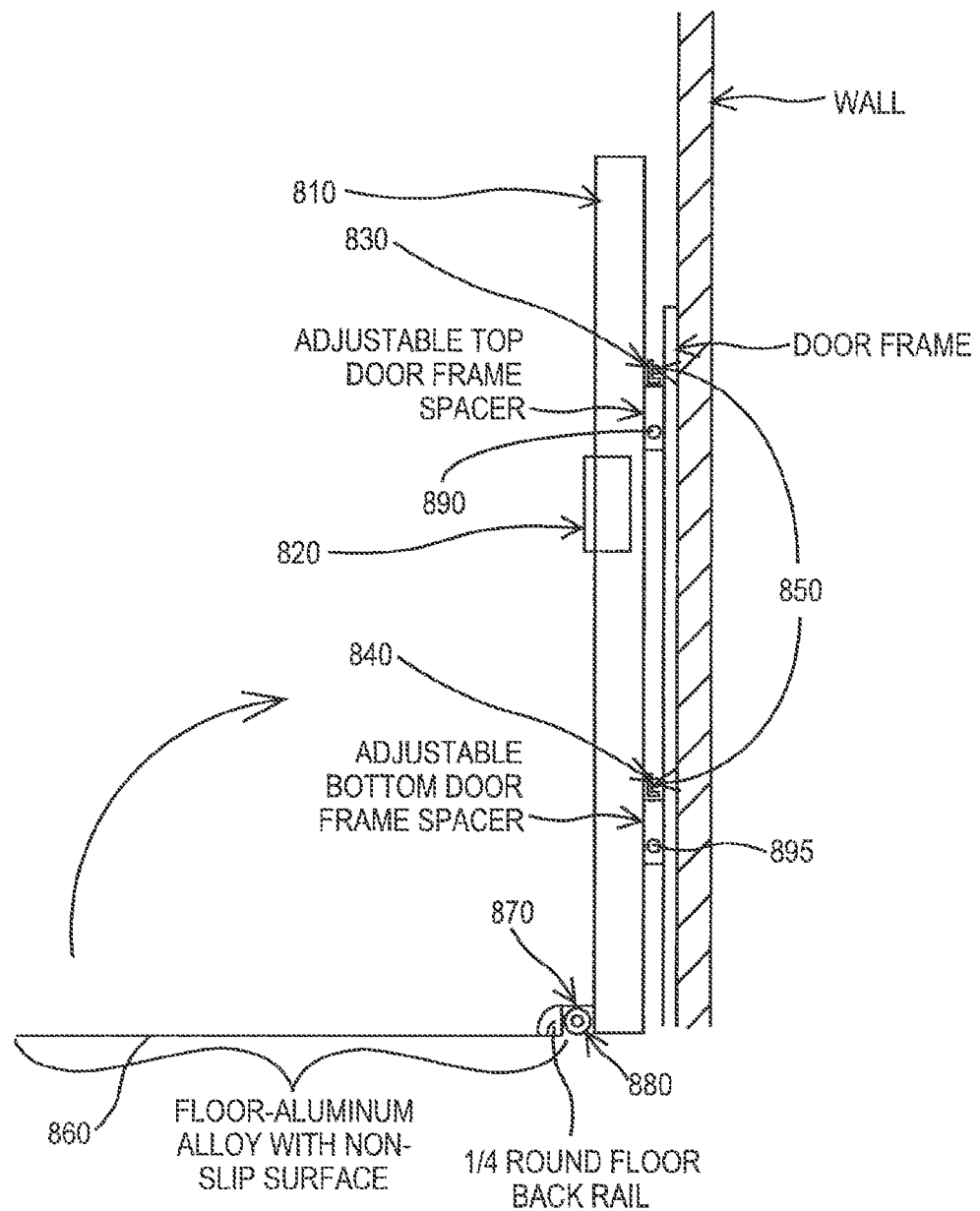
FIG. 8 is a side view of Applicants' Portable Door Hanger System.
Figure 26:
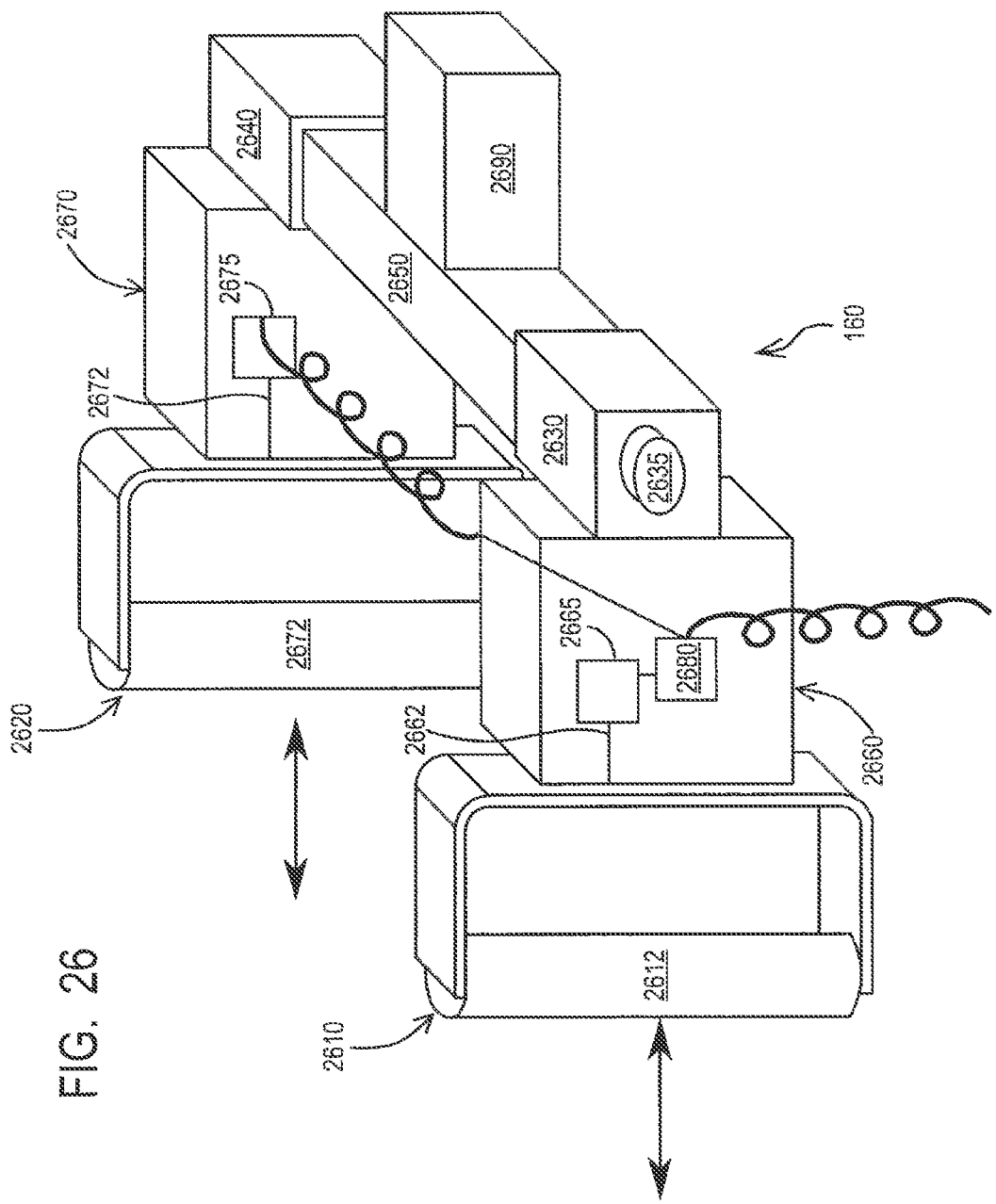
FIG. 26 is a perspective view of Applicants' Strength Push/Pull/Lift Device.

Referring now to FIG. 26, Applicants' Strength Push/Pull/Lift Device 160 comprises force handle assembly 2610 which includes gripping surface 2612, force handle assembly 2620 which includes gripping surface 2612, housing 2660, housing 2670, force handle base 2630, force handle base 2640, force arm 2650, and plate arm 2690. Plate arm 2690 can be removeably attached to monopole shuttle 820 (FIG. 8).

Force handle base 2630 is releaseably attached to force handle arm 2650 using thumb screw 2635. Force handle base 2640 is similarly releaseably attached to force handle arm using a thumb screw. In the first orientation of force handle assembly 2610 shown in FIG. 26, the test subject pushes or pulls gripping surface 2612 horizontally.

The first orientation of force handle assembly 2610 and/or 2620 shown in FIG. 26 can be adjusted to a second orientation by releasing thumb screw(s) 2635, one on each end of force arm 2650, repositioning the force handle assembly/housing 2660 and/or 2670 upwardly 90 degrees, and reattaching thumb screw(s) 2635. In this second orientation, the test subject pulls or lifts upwardly on gripping surface 2612 and/or 2622.

Similarly, the first orientation of force handle assembly 2610 and/or 2620 shown in FIG. 26 can be adjusted to a third orientation by releasing thumb screw(s) 2635, rotating force handle assembly/housing 2660 and/or 2670 downwardly 90 degrees, and reattaching thumb screw(s) 2635. In this third orientation, the test subject pushes or lifts upwardly on gripping surface 2612 and/or 2622.

Force handle assembly 2610 is attached to housing 2660. Bidirectional load cell 2665 is disposed within housing 2660, and is mechanically interconnected by member 2662 to force handle assembly 2610. Force handle assembly 2620 is attached to housing 2670. Bidirectional load cell 2675 is disposed within housing 2670, and is mechanically interconnected by member 2672 to force handle assembly 2620.

Load cell 2665 and load cell 2675 are interconnected with circuitry 2680. In certain embodiments, circuitry 2680 comprises circuitry 1400 (FIG. 14) wherein load cell 2665 is interconnected with ADC 1420 (FIG. 14), and wherein load cell 2675 is interconnected with ADC 1425 (FIG. 14). Circuitry 2680 and 2675 are releaseably interconnected with the host computer. In certain embodiments, circuitry 2680 interconnects with host computer via USB interface 1470 (FIG. 14).

Device 160 measures the strength over a specified time interval for a specified number of times programmable by the evaluator. Device 160 can also be used to measure force applied by only one hand by placing one of the measurement handles in the center of the device.

In addition to the static testing device described above, Applicants' system 100 further includes performance test devices 170, 180, and 190. These devices measure how well an individual performs work movements. Sensors are placed at various locations to monitor work movements and the time required to complete each move is recorded.

Applicants' Device 198 (FIG. 1B), which includes Devices 180 (FIGS. 1A, 1B) and 190 (FIGS. 1A, 1B), measures functional hand/eye coordination and hand/finger movement. Device 190 comprises an enclosure having the handling and proprioception tests on one side, and finger flexion test on another side. Device 198 is thereby an integrated device that permits one apparatus to replace at least two different devices required using prior art apparatus and methods. Referring again to FIG. 2, such integration allows both devices to use common elements 210, 220, 260, 270, and 280. In certain embodiments, device 198 includes two Touch Pads that share one Touch Interface.

Applicants' device 190 is used to measure the individual's fingering and handling performance as defined by the U.S. Department of Labor. Fingering is defined as the individual's ability to pick, pinch or otherwise work primarily with the fingers rather than the whole hand or arm. Fingering contains two test components when measuring this physical demand, finger flexion and proprioception. Applicants' Fingering/Handling Device 190 uses solid state components to prevent mechanical breakdown of components, thereby overcoming a problem inherent with prior art testing devices.

Applicants' Finger Flexion Device 180, when used for finger flexion testing, isolates the fingers from the hand, wrist, forearm and shoulder unlike prior art devices where an individual may compensate for finger movements by using the wrist, forearm or shoulder. Referring now to FIG. 3, Device 180 includes Finger Flexion Station 300 which maintains the hand, forearm, and body in a stationary position so that only the fingers move.

Finger Flexion Station 300 comprises Panel 305, Palm Rest Locations 310*a* and 310*b*, Touch Pad 320, Touch Pad Light 330, Finger Touch Pad 340, and Finger Touch Pad Light 350.

Device 180 measures the speed at which an individual can move his/her fingers repetitively. Prior art devices comprise a keyboard. Problems are inherent with these prior art devices because when using a keyboard the tested person must use different downward movements and bounce back movements, where those movements are a function of the mechanics of the keyboard being used. In addition, the mechanical aspects of keyboards age and change over time, and from manufacturer to manufacturer. Thus using such prior art devices and methods, little consistency exists between tests for the same individual.

In contrast, Applicants' Finger Flexion Device 180 does not vary with use or time, because use of station 300 does not include using a keyboard, but rather uses solid state touch technology. Using Applicants' station 300, no downward finger pressure is needed to record the flexion move. Individuals who have had joint replacement on a finger tend to rotate the wrist when applying downward finger pressure. Use of a keyboard device distorts the test for these persons. Applicants' design uses a touch pad with a large surface area and a cushion for the individual to rest his or her palm.

Applicants' Finger Flexion Station 300 isolates finger movement from wrist and arm movement. Using Applicants' apparatus and method, the individual moves only the fingers. The individual being tested does not have to apply finger pressure as with a keyboard. All that is needed is to make contact with the touch pad. This keeps the test from being distorted. The movements are monitored by the host computer to determine finger flexibility required to perform certain types of work.

In certain embodiments, Applicants' touch circuitry projects an invisible field capable of detecting the intrusion or contact of the human body into the sense field. The sense field is calibrated so that it causes a detection of intrusion when the enclosure surface is contacted. The sense field may also be calibrated for non-contact applications, for instance to detect the presence of the human body within 1 cm of the surface. Using such touch sense circuitry minimizes the stress applied to the operable body part which is desirable when there is pathology or injury to that body part. Since the sense circuitry requires no force, this minimizes pain or discomfort associated with the testing apparatus. Such a sense circuit is available from Q-Touch, Inc.

Handling, as defined by the U.S. Department of Labor, is described as the individual's ability to seize, hold, grasp, turn or otherwise work with the hand or hands. In the definition of handling, fingers are involved only to the extent that they are extensions of the hand, such as to turn a switch or shift automobile gears.

Handling/Proprioception Device 190 includes an element to measure proprioception via the movement of a pin from one location to another, and handling via rotating or inverting and placing a faceted object. Proprioception as related to work function is defined as the individual's ability to recognize where the body part is by way of feedback to biofunctional receptors located in the muscles, tendons, joints and skin.

Because fingering requires precise motor control to perform work, proprioception and finger flexion performance is commonly used to determine this physical capacity. The ability to pick, move and manipulate small items using visual queues has become the most common method of assessing proprioception. In addition to functional motor control, the individual must have adequate hand/eye coordination to complete the moves.

Prior art devices and methods to measure this physical performance are problematic. The most common prior art methods employ a simple wood pegboard requiring the person being tested to insert pins or pegs as fast as possible in a series of holes. These prior art tests are typically short timed activities, non-isolative, and do not sufficiently load the muscles of the hand and fingers to predict future work performance.

In contrast, Applicants' proprioception device requires the individual to repeat exactly the same moves throughout the test activity lasting approximately 10 times longer than current tests. This makes it easily compatible with Method-Time Measurement time and motion performance scoring.

Figure 9:
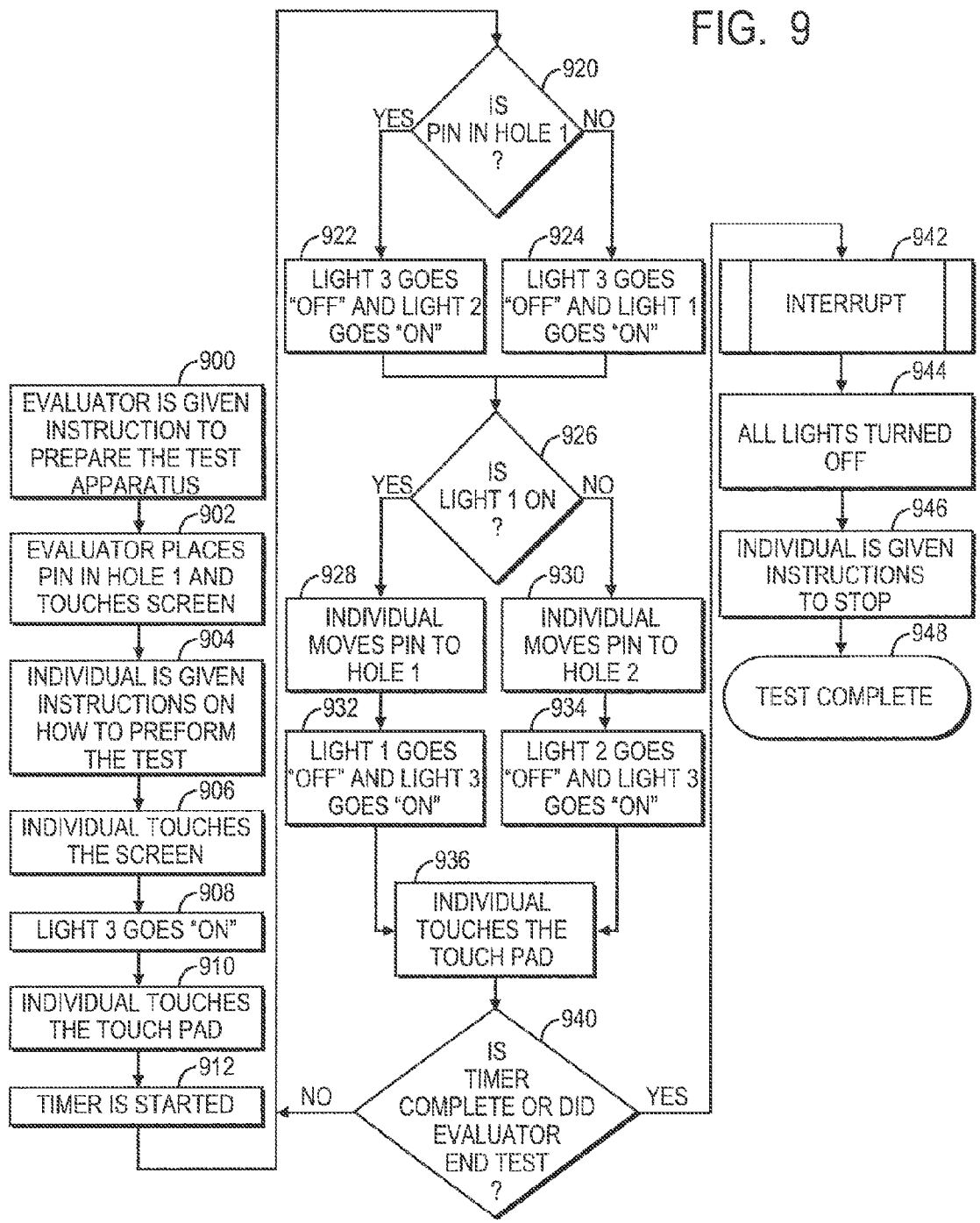
FIG. 9 is a flow chart summarizing the steps of Applicants' Proprioception Test Sequence.

FIG. 4 shows Applicants' proprioception test station 400, which is an element of Device 190. FIG. 9 summarizes Applicants' proprioception test sequence. Handling/Proprioception test station 400 is formed to include apertures 410, 455, 465, 475, and 485, and further comprises panel 405, Touch Pad 420, Touch Pad Light 430, faceted object 440 dimensioned to fit within aperture 410, first light 450 disposed adjacent aperture 455, second light 460 disposed adjacent aperture 465, third light 470 disposed adjacent aperture 475, and fourth light 480 disposed adjacent aperture 485.

Using Applicants' proprioception test, an individual moves a pin from one location to another, i.e. between apertures 455, 465, 475, and 485. The protocol defines a time period required to perform the tests. An evaluator sets up the test and the individual operates an actuator. In certain embodiments, the individual touches a touch pad, which has a sensor, to start the test and record various movements.

During the test sequence, an individual touches touch pad 420, moves his hand from the touch pad to a pin, grasps the pin, picks up the pin, and moves the pin from one or apertures 455, 465, 475, and 485, to a different one of those apertures. At the bottom of each of apertures 455, 465, 475, and 485 is a metal plate. The individual must hold the pin until it reaches that metal plate in order for the test move to be complete. Touching the metal plate generates a signal. This signal is monitored by the host.

The pin cannot be dropped into the aperture to complete the test. Rather, the pin must be held by the individual until it reaches metal plate disposed at the bottom of the aperture.

This then results in a pure controlled movement with a more accurate read of the move. The host computer monitors the test for completion and speed using two sensors. The hand is moved back to the touch pad which is touched to complete the test cycle. The test routine is repeated until the timing is complete. Applicants' method can comprise a repetitive test where it is run for a predetermined number of repetitions, or for a predetermined time. In certain embodiments, Applicants' method further includes screwing the pin into the hole, or placing a pin into a shaped hole such as a triangle or square.

In certain embodiments, Applicants' device 198, which includes Device 180 and Device 190, further includes elements 210, 220, 260, 270, and 280 recited in FIG. 2. The control circuitry 210 disposed within device 300 detects the contact of the human body by measuring the change of capacitance or inductance of a metal plate when touched. This change creates a measurable electrical signal which is amplified and conditioned to simulate the function of a mechanical switch. If a body part required to touch the plate is not able to do the touch by skin contact, with the touch plate, due to being in a cast or another reason, conductive material is worn surrounding the required body part and touching the skin elsewhere. This allows the test to proceed as normal.

Referring again to FIG. 4, station 400 further includes faceted object 440. In certain embodiments, object 440 comprises a cube which can be removeably inserted into aperture 410 in as many as twenty-four (24) different orientations, i.e. six faces times four different orientations per face. The surfaces of the object are marked with letters or other symbols. Applicants' test includes several test sequences as follows: an individual presses a touch pad at the start of the test which has a LED "on" above it. The touch turns "off" the LED and an object move is instructed. In one test the individual picks up the object and rotates the object to a predetermined position. In another test the individual inverts the object. In another test the individual rotates and inverts the object.

In another test the individual starts with the object at a predetermined position, for example the letter "A" showing upward, then moves the object to a position with some other letter in the upward position. After completing the correct move, the touch pad again lights and the individual presses the touch pad to complete the test move. The activity is repeated for the next requested move and so on. These tests can be run as a serial test with any combination of the above tests. In certain embodiments, Applicants' handling device and method senses both which letter or symbol is on top, but also which direction the letter or symbol is facing.

Figure 10:
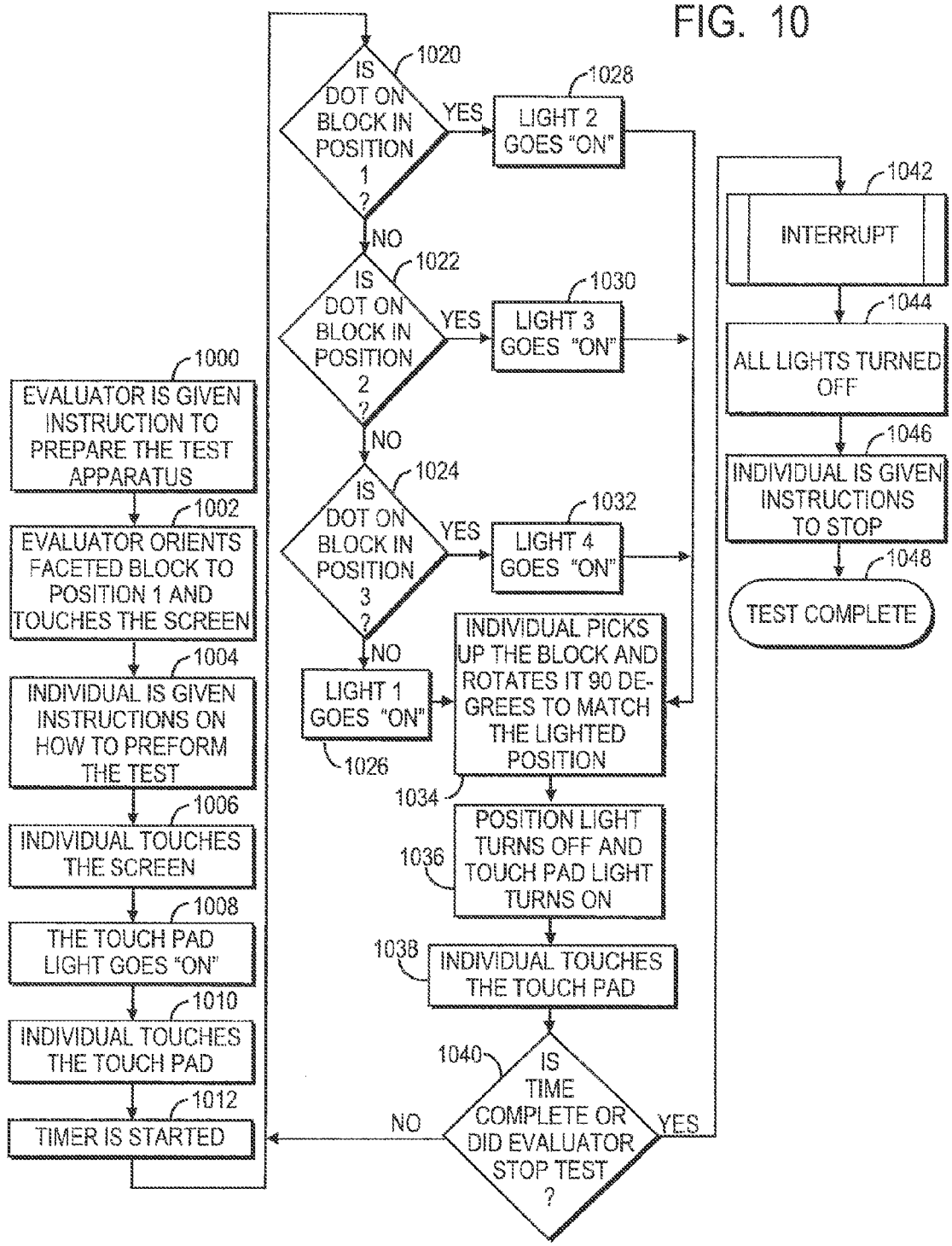
FIG. 10 is a flow chart summarizing the steps of Applicants' 90 Degree Rotation Test Sequence.

FIG. 10 summarizes Applicants' handling test sequence. The handling test measures a more gross movement of a faceted object into a square hole. Here an object is turned 90, 180 or 270 degrees, or the object is flipped to the upside down position and may be turned. For this test an evaluator sets up the test and the individual touches the screen to start the test. An LED goes "on" near the touch pad. The individual touches the touch pad with his thumb or designated body part and the first LED goes "off" then one of four LEDs, located at each corner of the hole, go "on". When the individual completes the rotation or flip operation correctly the LED goes "off" and the touch pad LED goes "on". The host computer reads the correct position when the object is placed back in the hole by reading a set of magnets in the target. After the object is replaced, the individual makes the next move using his or her thumb or designated body part to touch the pad. The test is run repetitively for a predetermined amount of time which completes the test. The host monitors the test for correctness and monitors the speed.

Applicants' test more precisely quantifies pick and place movement than do prior art devices and methods. In certain embodiments, Applicants' sensing system comprises one or more magnets in combination with one or more magnetic reed switches or hall-effect sensors which are very low power. In other embodiments, Applicants' sensing system comprises photo sensors.

As those skilled in the art will appreciate, handling is a common move performed in the manufacturing environment. In certain embodiments, Applicants' handling test further includes operations where the object is rotated or flipped so that any of the six identifiable faces of the object is in the top position. In certain embodiments, Applicants' handling test further includes operations where the object is rotated or flipped so that any of the six identifiable faces of the object is in the top position and is pointing in a predetermined direction.

Figure 19:
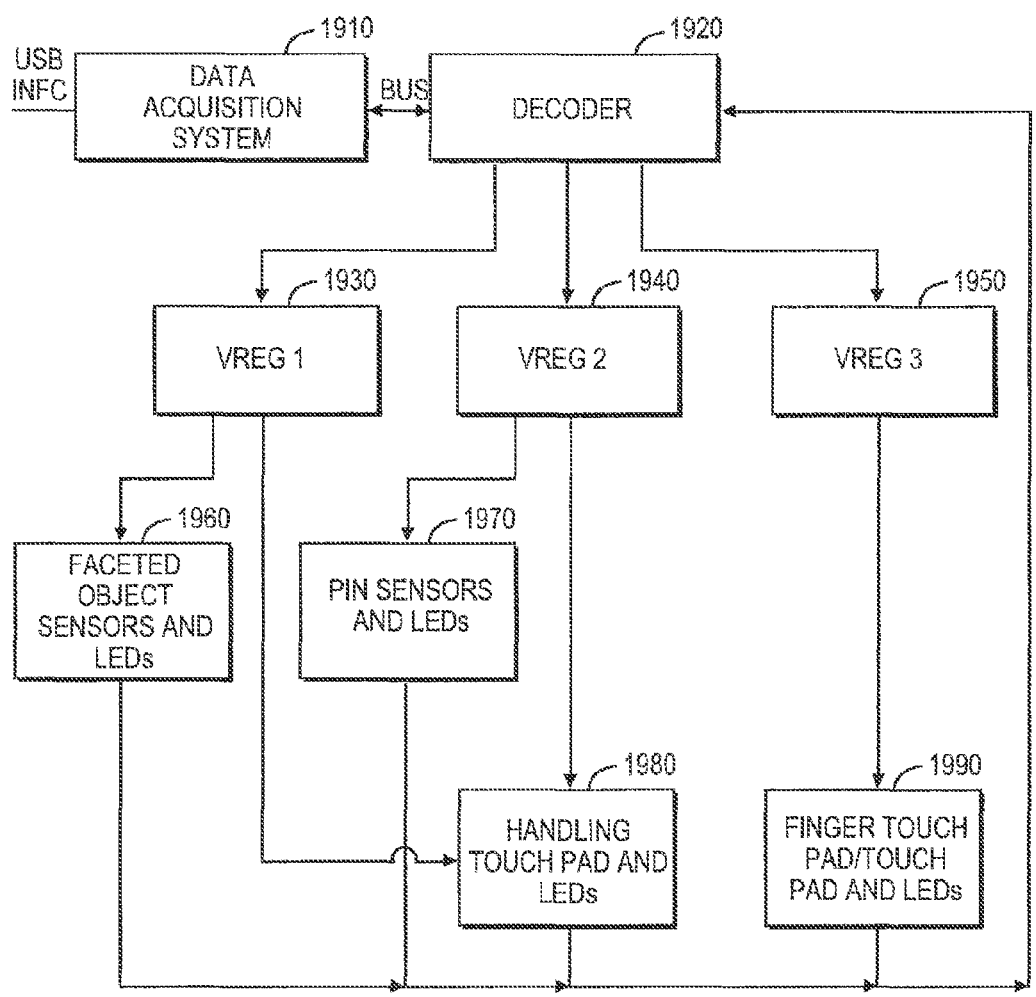
FIG. 19 is a block diagram showing the electrical components of Applicants' Finger Flexion Device 180 and Handling/Proprioception Device 190.

FIG. 19 shows the control elements for Applicants' Finger Flexion Device and Handling/Proprioception Device. In certain embodiments of Applicants' apparatus, the circuits for Applicant's Finger Flexion Device and the Handling/Proprioception Device, except for a Data Acquisition System (DAQ) with USB interface such as Data Acquisition System circuit 1910, are packaged together. Referring to FIG. 19, Data Acquisition System circuit 1910, which comprises a USB data acquisition system, provides a USB interface for host connection. Data Acquisition System circuit 1910 is connected to Decoder 1920 which selects voltage regulators VREG1, VREG2 and/or VREG3. When a voltage regulator is turned "on" by the Data Acquisition System, it turns "on" the power to the sensors and LEDs associated with that voltage regulator.

In certain embodiments, if VREG3 is turned "on," Applicants' Finger Flexion circuitry is turned "on". Faceted Object Sensors and LEDS circuitry 1960 comprises the hardware needed to read the orientation of the facetted block, and provides the LED feedback to the person being tested. The PIN Sensors and LED circuitry 1970 provides the sensing and LED response associated with pin placement in holes 1 through 4 as shown in FIG. 4.

The Handling Touch Pad and LED circuitry 1980 comprises the sensing and LED response required when a user touches the Handling Touch Pad shown in FIG. 4. The Finger Touch Pad and Touch Pads and LEDs circuit 1990 comprises the circuitry needed for the Finger Flexion test. Circuitry 1990 comprises the sensing function for the Finger Touch Pad, the sensing function for the Touch Pad and the LED response as shown in FIG. 3.

Figure 20:
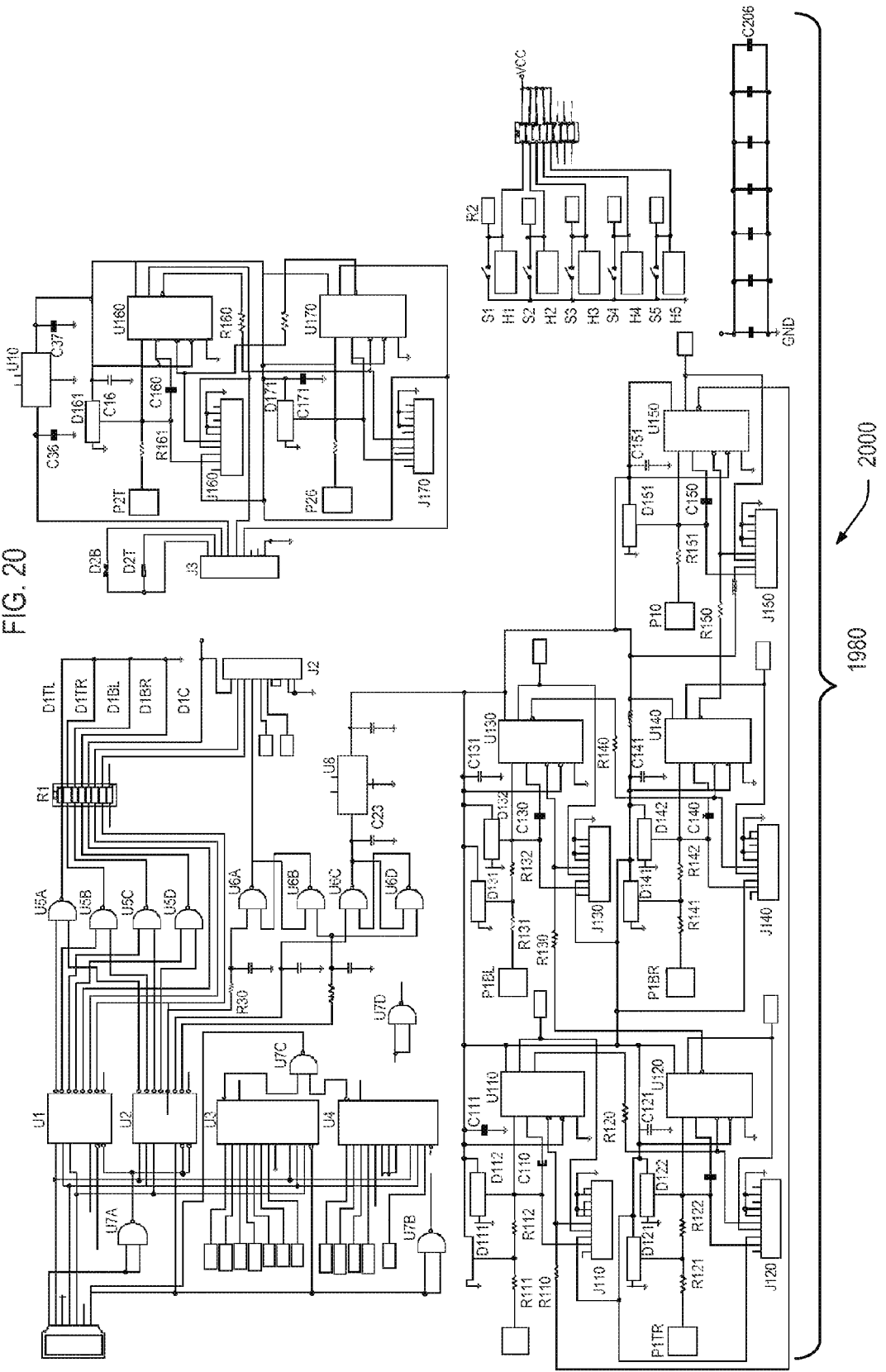
FIG. 20 is a circuit diagram showing circuitry to implement the components of FIG. 19.

In certain embodiments, the elements of FIG. 19 are implemented using circuitry 2000 shown in FIG. 20. Circuitry 2000 includes Decoder circuitry portion 1920, Handling Touch Pad and LED circuitry 1980, Finger Touch Pad/Touch Pad and LED circuitry 1990. FIG. 19 VREGs are distributed throughout the FIG. 20 circuitry. In other embodiments, FIGS. 19 and 20 are made an integrated device by removing Data Acquisition System 1910 and adding circuitry 1410, 1450, 1460, 1470, and 1480 from FIG. 14.

Figure 11:
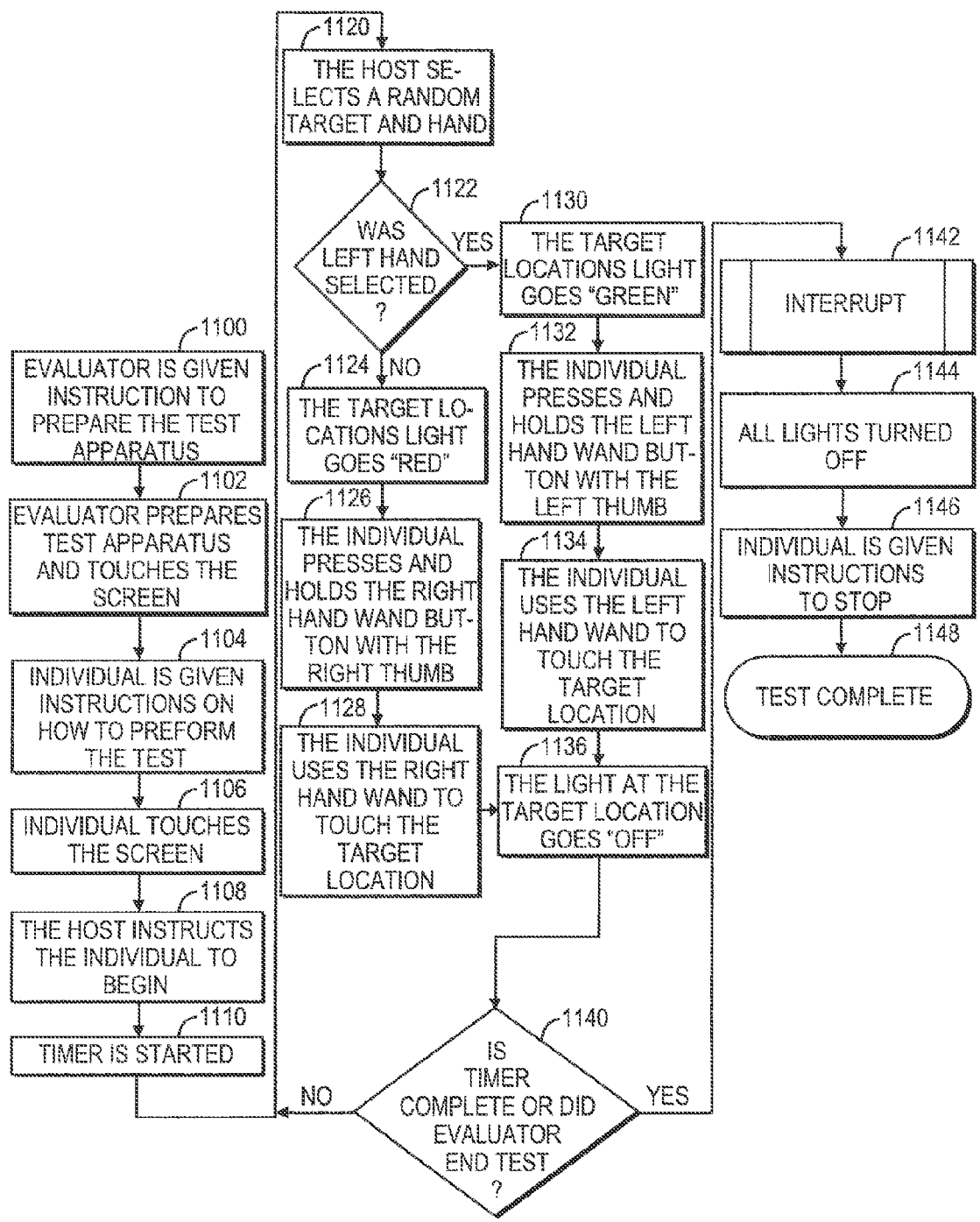
FIG. 11 is a flow chart summarizing the steps of Applicants' Whole Body Coordination Test Sequence.

Applicants' Whole Body Coordination Device 170 measures gross and fine motion of the upper extremity (ies), usually while standing, stooping, crouching or kneeling positions among others. Referring now to FIGS. 5, 23, and 11, FIGS. 5 and 23 illustrate embodiments of Applicants' whole body coordination device 170. FIG. 11 summarizes Applicants' whole body coordination test. When performing this test, the individual holds a wand in both hands and responds to a dual colored LED light stimulus and/or commands from the host. If the LED is "red", the individual touches the touch pad or sensing area next to the lit LED with the wand in his right hand. If the LED is "green", the individual touches the touch pad or sensing area next to the lit LED with the wand in his left hand. The test is run repeatedly for a designated time interval.

The wands are used to reach forward, downwardly, or upwardly, and touch particular points consisting of touch pads or sensing areas on a touch panel in front of the individual. The points are located on a vertical surface that can also be positioned horizontal and/or overhead. The individual must make a functional grasp of the wand at the beginning of the test, and must continue to maintain the functional grasp when touching the wand to the touch pads or sensing areas throughout the test. The functional grasp used with this device is defined as an oblique grasp. An oblique grasp is used to hold a screwdriver or an open wrench. In this case the wands are held with the individual's thumb applying a predetermined pressure to a button switch that closes a circuit for monitoring purposes. In certain embodiments, Applicants' default protocol for the test is set up to guarantee that the individual moves the wands to every combination of positions.

Applicants' wands are configured in various shapes and grip pressures to match job standards or demands. Grip sizes, and types can be used on the wands that match the job or measurement requirement(s). Other grip options include circular, lateral, precision, and other types. A circular grasp is used, for example, when holding a hand tool. A lateral grasp is used, for example, when holding a flat object like sheet steel with the thumb applying hold pressure on the top side and the fingers on the opposite side of the object. A precision grasp is used, for example, when holding an object with opposition pressure between the tips thumb and typically the index and middle fingers.

Applicants' grip wands assure that the specific upper extremity physical or work demand needed is being used to make each movement in the test. The host computer uses test information to determine the individual's functional work capacity. The test is a whole body test that monitors the functional work posture of the individual. For example, if an individual has poor mobility in the elbow, it can be compensated for by turning at the waist instead of bending the elbow to touch the appropriate point. This can affect the performance of the individual but not necessarily the capacity of the individual to perform the test. In certain embodiments, Applicants' method includes using tests that requirement movement of both wands at the same time or sequentially. For example, these test protocols could be used as a training device for pilots who are required to perform moves with both hands at the same time.

Applicants' Whole Body Coordination Device 170 can be used for work hardening or conditioning where an individual is tested to improve his or her postural strength or functional work range abilities. Here the test is performed many times in succession for a long period of time. The host monitors the performance and documents improvement, fatigue patterns, concentration and other related work demands. The protocols can be customized by the evaluator to meet the needs of an individual case.

In the illustrated embodiment of FIG. 5, Applicants' Whole Body Coordination Device 170 comprises panel 502. In certain embodiments, panel 502 is approximately 3 feet wide by 2 feet high with a hard non-conductive surface. Whole Body Coordination Device 170 further comprises a plurality of metal disks, touch pads, each having a light disposed adjacent on the panel surface.

In the illustrated embodiment of FIG. 5, Applicants' Whole Body Coordination Device 170 comprises touch pads 522, 523, 524, 525, 526, 527, 542, 543, 544, 545, 546, 547, 562, 563, 564, 565, 566, 567, 582, 583, 584, 585, 586, and 587. In the illustrated embodiment of FIG. 5, Applicants' Whole Body Coordination Device 170 comprises lights 532, 533, 534, 535, 536, 537, 552, 553, 554, 555, 556, 557, 572, 573, 574, 575, 576, 577, 592, 593, 594, 595, 596, and 597, which can be located above, below, adjacent or within the associated touch pads.

In the illustrated embodiment of FIG. 5, the light associated with each touch pad is disposed below that touch pad. In other embodiments, the light associated with each touch pad is disposed above that touch pad.

Applicants' Whole Body Coordination Device 170 further comprises wands 510 and 515. In certain embodiments, wand 510 and 515 are tubular or other shaped wands. Wand 510 is flexibly interconnected with panel 502 via flexible communication link 504. Wand 515 is flexibly interconnected with panel 502 via flexible communication link 505.

Wand 510 comprises shaft 512, thumb button/grip sensor 513 disposed on shaft 512, light 511 disposed on shaft 512, and conductive end 514 which the user touches to the panel's various metal disks as part of the test, rehabilitation, human performance or work performance activity. Wand 515 comprises shaft 517, thumb button/grip sensor 518 disposed on shaft 517, light 516 disposed on shaft 517, and conductive end 519.

When the user presses the wand's thumb button or activates the grip sensor, the light on the wand turns on and its sensing circuit becomes active. The participant user touches each disk with the appropriate wand as the light associated with that disk is lit. The panel lights can emit two different colors. The user responds by pressing the corresponding wand thumb button or activating the grip sensor to activate the sensing circuit for that hand, and touches the metal disk below the light. For example, in certain embodiments a red light indicates use of the right-hand wand and a green light indicates uses of the left-hand wand. When the correct metal disk is touched with the wand, that light turns off and the next programmed light on the panel turns on. This sequencing of lights continues for the duration of the programmed activity, and the results are recorded for use by the computer, microprocessor or other electronic recording device for interpretation by an operating program.

In certain embodiments, the panel is connected to a shuttle that permits adjustment of the panel vertically on a monopole, thereby allowing the panel to be used at different heights. The shuttle connecter is constructed to allow the touch panel surface to be used in a vertical orientation or a horizontal orientation wherein the user surface faces the floor. Changing the panel from a vertical to a horizontal orientation is accomplished by pulling the top edge of the panel to release a magnetic connector on the panel back from the shuttle connector. A hinge allows the panel to rotate to the horizontal position with the assist of a fixed force gas spring, which also stabilizes the panel during horizontal use.

The panel can be adjusted from the horizontal orientation to the vertical orientation by lifting the leading edge up and rotating back toward the monopole until the back connects with the magnetic connector on the shuttle connector. In other embodiments, the panel may also be positioned horizontally with the sensing surface facing the ceiling for assessing the work surface response of the user participant. In other embodiments, the panel may be positioned at custom plane angles to match specific job demands. In other embodiments, the panel can emit three colors instead of two colors. When a third color is emitted, the evaluee touches the metal disk with both left and right wands.

FIG. 23 illustrates a second embodiment of Applicants' Whole Body Coordination Device 170. This embodiment comprises panel 2302, wand 510 (FIG. 5), flexible interconnection 504 (FIG. 5), wand 515 (FIG. 5) and flexible interconnection 505 (FIG. 5). Panel 2302 comprises a smooth, translucent surface with no visible features. By "translucent surface," Applicants mean that light emitted by each of the plurality of LEDs disposed behind panel 2302 is visually detectable by a person standing adjacent the exterior surface of panel 2302.

Behind the surface of the panel is circuitry comprising LED lights disposed behind the panel surface at various locations. The illustrated embodiment of FIG. 23 comprises LEDs 532, 533, 534, 535, 536, 537, 552, 553, 554, 555, 556, 557, 572, 573, 574, 575, 576, 577, 592, 593, 594, 595, 596, and 597.

The LEDs can emit three colors, namely red, green or white. The LEDs are controlled by the computer, microprocessor or other electronic controller. An electromagnet surrounds each LED, and that electromagnet is activated when the LED is on. The illustrated embodiment of FIG. 23 comprises electromagnets 2322, 2323, 2324, 2325, 2326, 2327, 2342, 2343, 2344, 2345, 2346, 2347, 2362, 2363, 2364, 2365, 2366, 2367, 2382, 2383, 2384, 2385, 2386, and 2387. Each electromagnet comprises substantially the same diameter as the metal disk touch pads of FIG. 5 described above.

Interconnected with the panel at the left and right lower corners of the panel are two tubular wands 510 (FIG. 5) and 515 (FIG. 5) described above. When the user presses the wand's thumb button or activates the grip sensor, the light on the wand lights and its sensing circuit, a Hall Effect sensor, is active. The participant user responds to each of the LED locations by touching the panel at the emitting LED with the corresponding wand. The panel lights can emit three different colors. The user responds by depressing the corresponding wand thumb button or activating the grip sensor to activate the sensing circuit for the indicated hand, and touches the light location. When the correct light area is touched with the wand(s,) that LED turns off and the next programmed light on the panel turns on. This continues for the duration of the programmed activity, and the results are recorded for use by the computer, microprocessor or other electronic recording device for interpretation by an operating program. Both touch panel versions are connected to the monopole using the same hardware.

Figure 17:
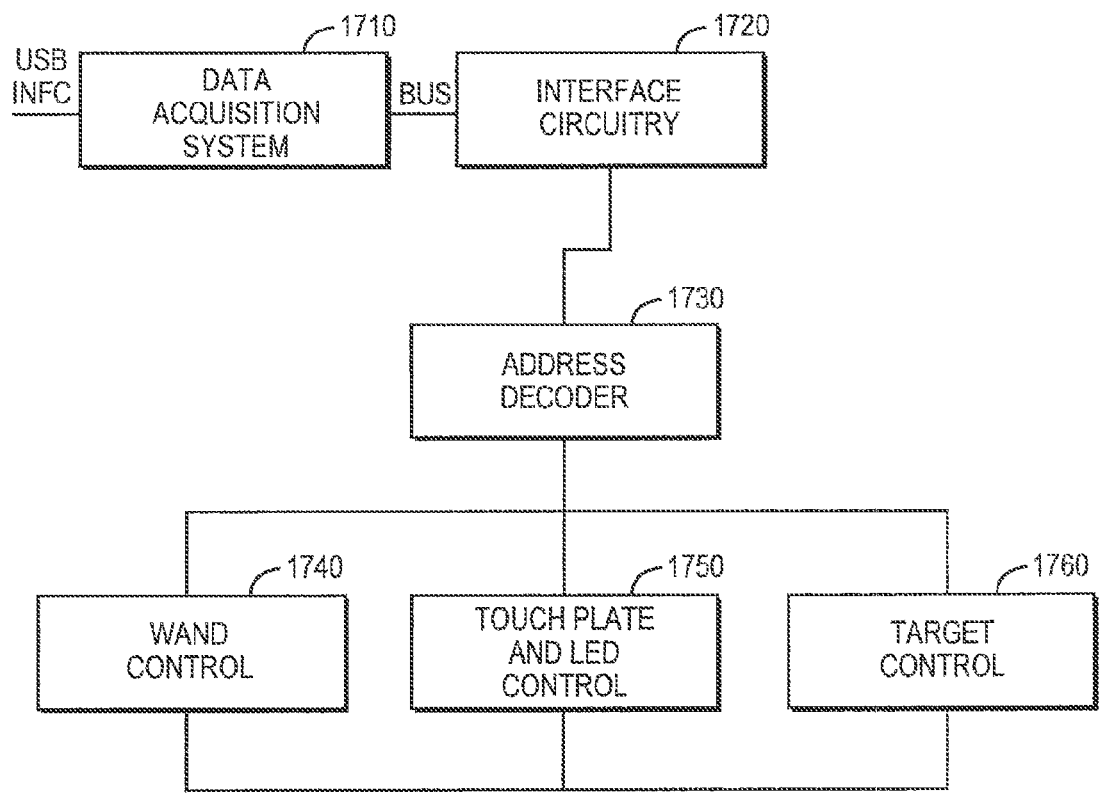
FIG. 17 is a block diagram showing the electrical components of Applicants' Whole Body Coordination Device.

FIG. 17 shows the elements used to operate Applicants' Touch Panel. Data Acquisition System circuit 1710, which comprises a USB data acquisition system, provides a USB interface for the host computer connection. The Data Acquisition System circuit 1710, through Interface Circuitry 1720, connects to Address Decoder 1730 which selects either the Wand and/or the Touch Plate and LED. Wand Control 1740 determines which wand has been selected by the user and determines if the wand is touching the predetermined target. The Touch Plate and LED circuitry 1750 senses which Touch Plate has been touched and the turns on or off the associated LED. Target Control 1760 performs the same functions as 1750 for the target panel.

Figure 18:
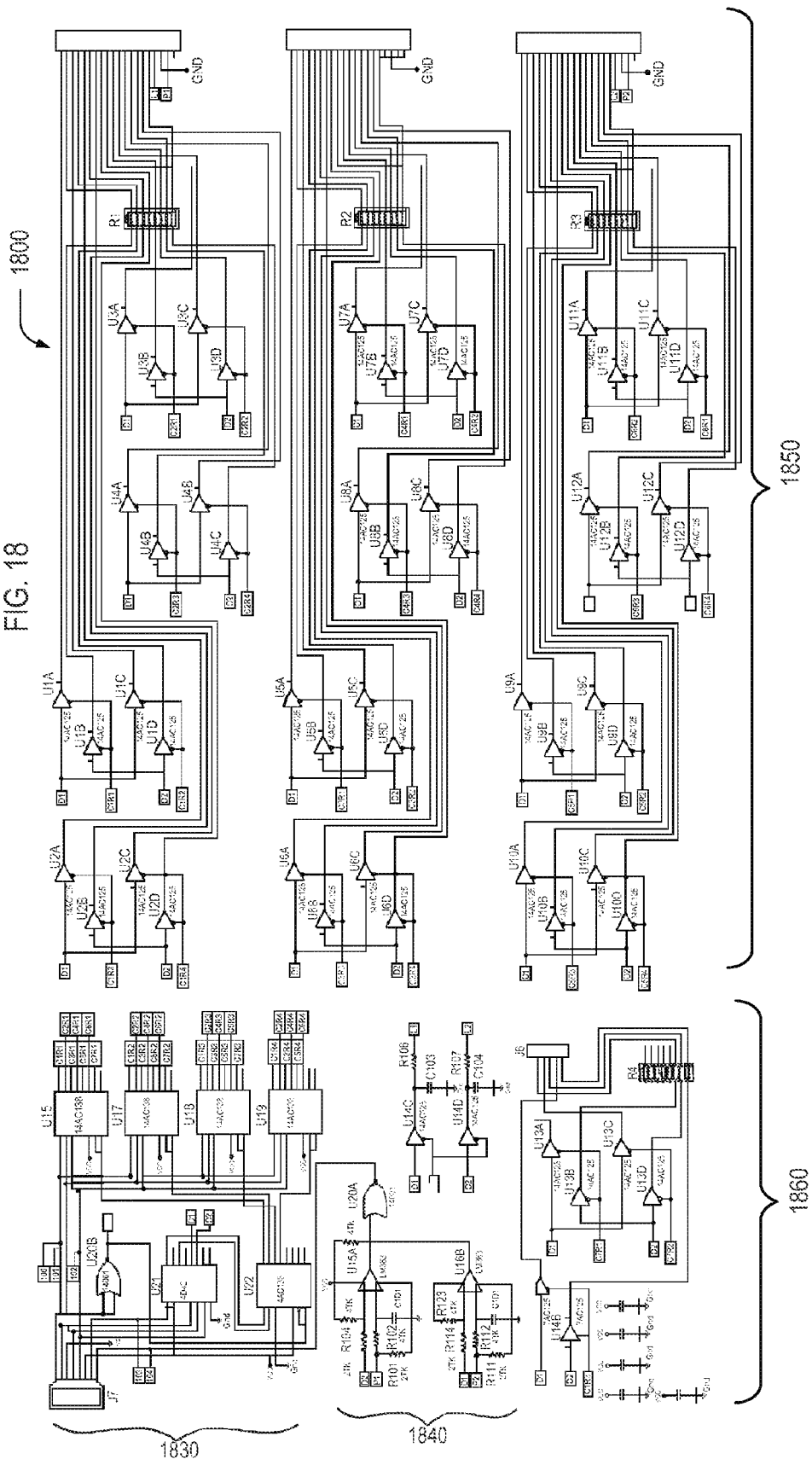
FIG. 18 is a circuit diagram showing circuitry to implement the components of FIG. 17.

The elements of FIG. 17 are implemented using circuitry 1800. Referring now to FIG. 18, circuitry 1800 includes portion 1830 comprising the Address Decoder, portion 1840 comprising the Wand Control, portion 1850 comprising the Touch Plate and LED Control and portion 1860 comprising Target Control. In other embodiments, FIG. 17 is made an integrated device by removing Data Acquisition System 1710 and adding circuitry 1400, 1410, 1450, 1460, 1470, and 1480 from FIG. 14.

Dynamic strength testing measures functional material handling of a worker. Applicants' system includes one dynamic strength device which comprises Applicants' Dynamic Lifting and Carrying Device 120.

Figure 24:
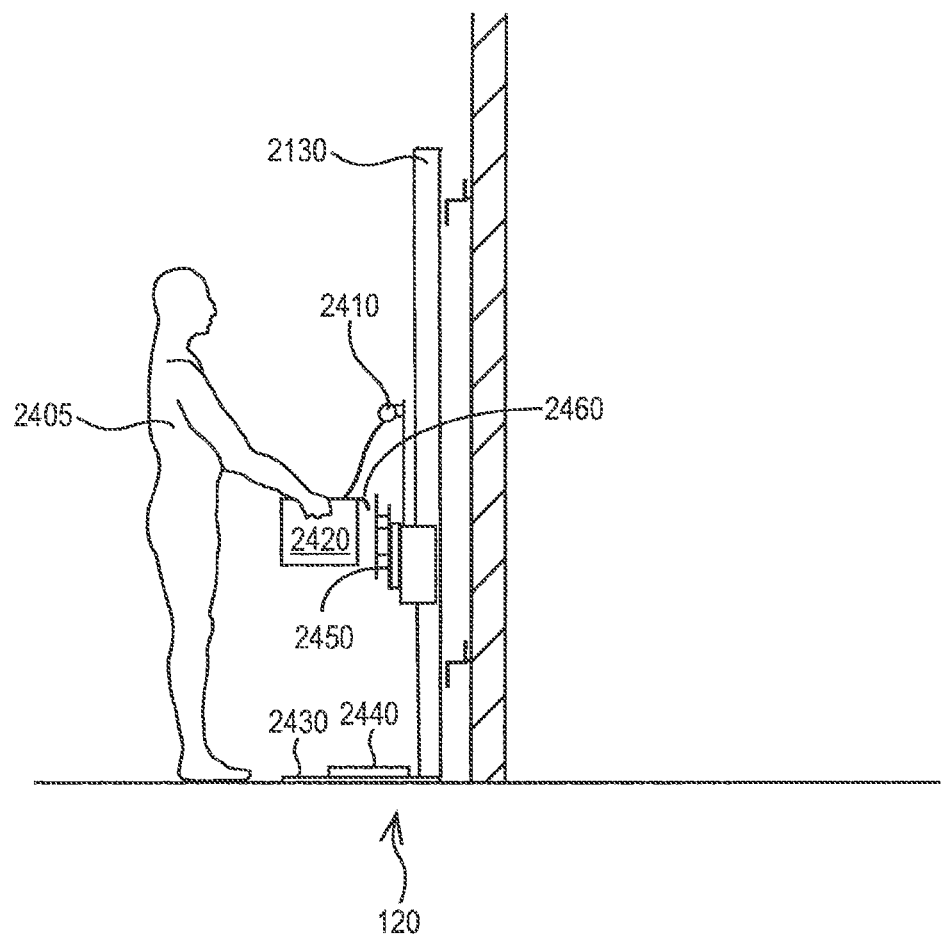
FIG. 24 is a side view of Applicants' Dynamic Strength Lifting and Carrying Device.
Figure 25:
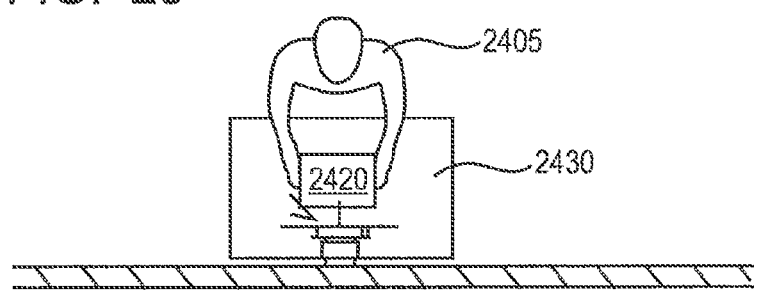
FIG. 25 is an overhead view of the apparatus of FIG. 24.

Referring now to FIGS. 24 and 25, Applicants' Dynamic Strength Test Device 120 is used to measure an individual's dynamic lift capacity. Lift velocity is measured using potentiometer 2410 which is interconnected with lift container 2420. Lift container 2420 comprises retainer angle 2460.

Scale 2440 is disposed on floor component 2430. Lift container is initially placed on scale 2440. The evaluee lifts container 2420 and removeably attaches that lift container to lift plate 2450 by hooking retainer angle 2460 over the top portion of lift plate 2450.

Prior art devices disposed a potentiometer in the floor portion of the testing apparatus. Because Applicants' potentiometer 2410 is attached to monopole 2130, Applicants' floor component is thinner, lighter and optional. Therefore unlike prior art test devices, Applicants' Dynamic Strength Test Device is portable.

Figure 27:
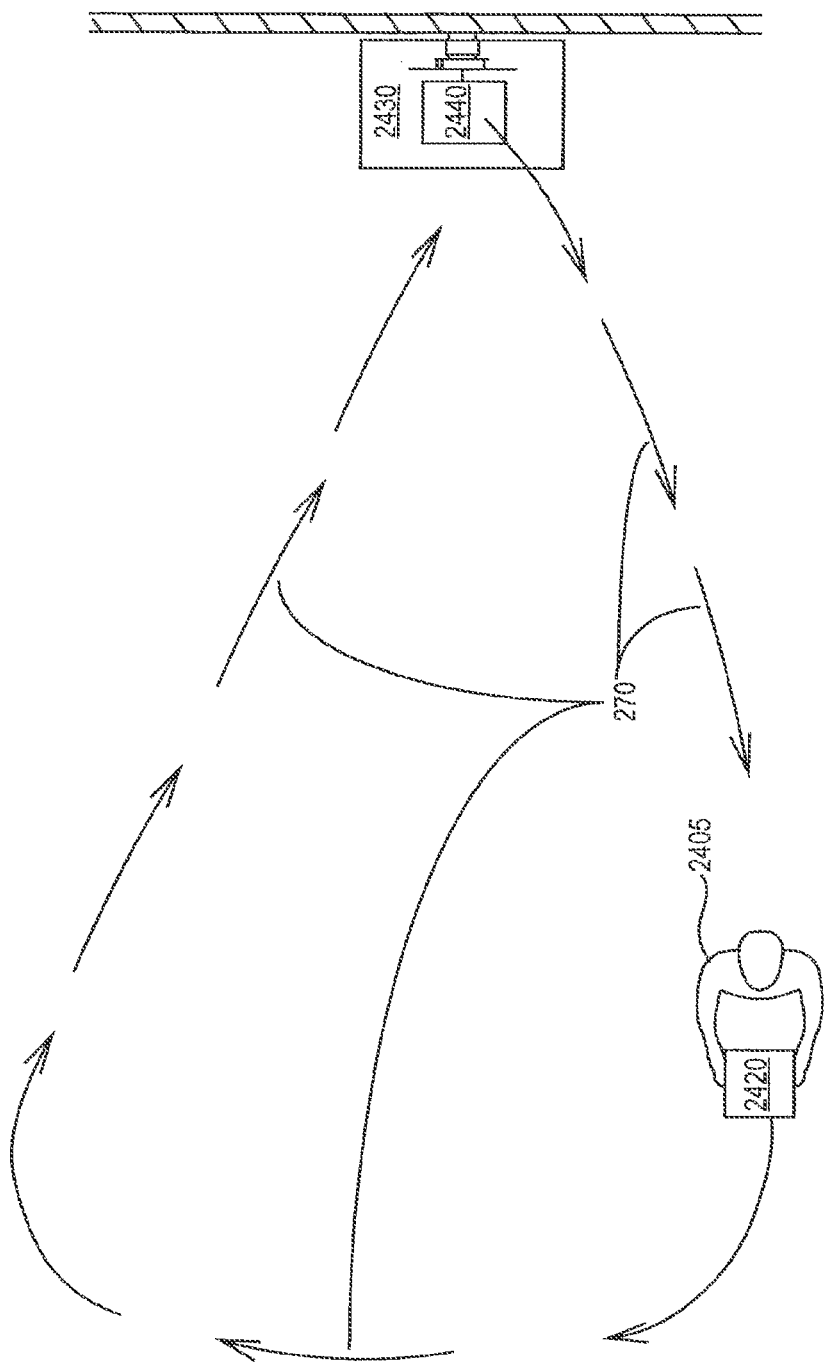
FIG. 27 is an overhead view of a Carrying Test implemented using the apparatus of FIG. 24.

Referring now to FIG. 27, Applicants' Dynamic Strength Test Device 120 can be further utilized to implement a carrying routine wherein evaluee 2405 lifts container 2420 from scale 2440, carries that lift container 2420 around a designated track 2710, and returns the lift container to scale 2440. The carry time is recorded by the host computer, and that recorded time is compared to MTM standards for competitive work performance.

Applicants' method provides an evidentiary record of the test activities recorded. The default lift object is a standard fiberglass tote box commonly used in industry for material handling. This tote box includes a simple hook across the back side of the box that can be attached to the lift destination. The lift destination is a flat vertical plate set by the evaluator as required to match the job standard or measurement requirement. During the test, the individual lifts the tote box and hooks it when prompted for a pre-set number of times and continues to lift greater weights until no longer safe or a lift standard is met depending on the test goals.

Applicants' Dynamic Strength Lifting and Carrying Device 120 measures dynamic whole body lifting and carrying strength. An Individual grasps a weighted object connected to a sensor with both hands. The device then measures the weight of the object, the velocity and distance of the lift. This test can be repeated with different increasing weights until the test goals are met.

When used for work hardening or conditioning, the device is used with a small range of increasing and decreasing weight. The system can be set to have an individual work for pre-set periods of time using prescribed weights and frequencies of lift. Such routines are used to improve human work performance at levels safely tolerable by the individual. As the individual meets performance standards, the host automatically resets the activity to the next performance routine until the prescribed goals are met.

As those skilled in the art will appreciate, a protocol is a process for performing a test or a series of tests in a standardized way so that the results reliably predict an individual's work capacity. Applicants' software administers the test according to the protocol. That software issues script elements required by the protocol, and executes the test in a manner defined by the protocol.

In certain embodiments, Applicants' method provides messages visually on a display, and audibly through earphones or speakers, to instruct the individual being tested. In addition, Applicants' software analyzes the data generated in a pre-determined manner to provide reliable and predictable conclusions. Test protocols can be customized by the evaluator to meet the needs of an individual. In certain embodiments, software interface screens are used to customize the protocol chosen by the evaluator, defined by job analysis, required by the user or required for other reasons.

Figure 12:
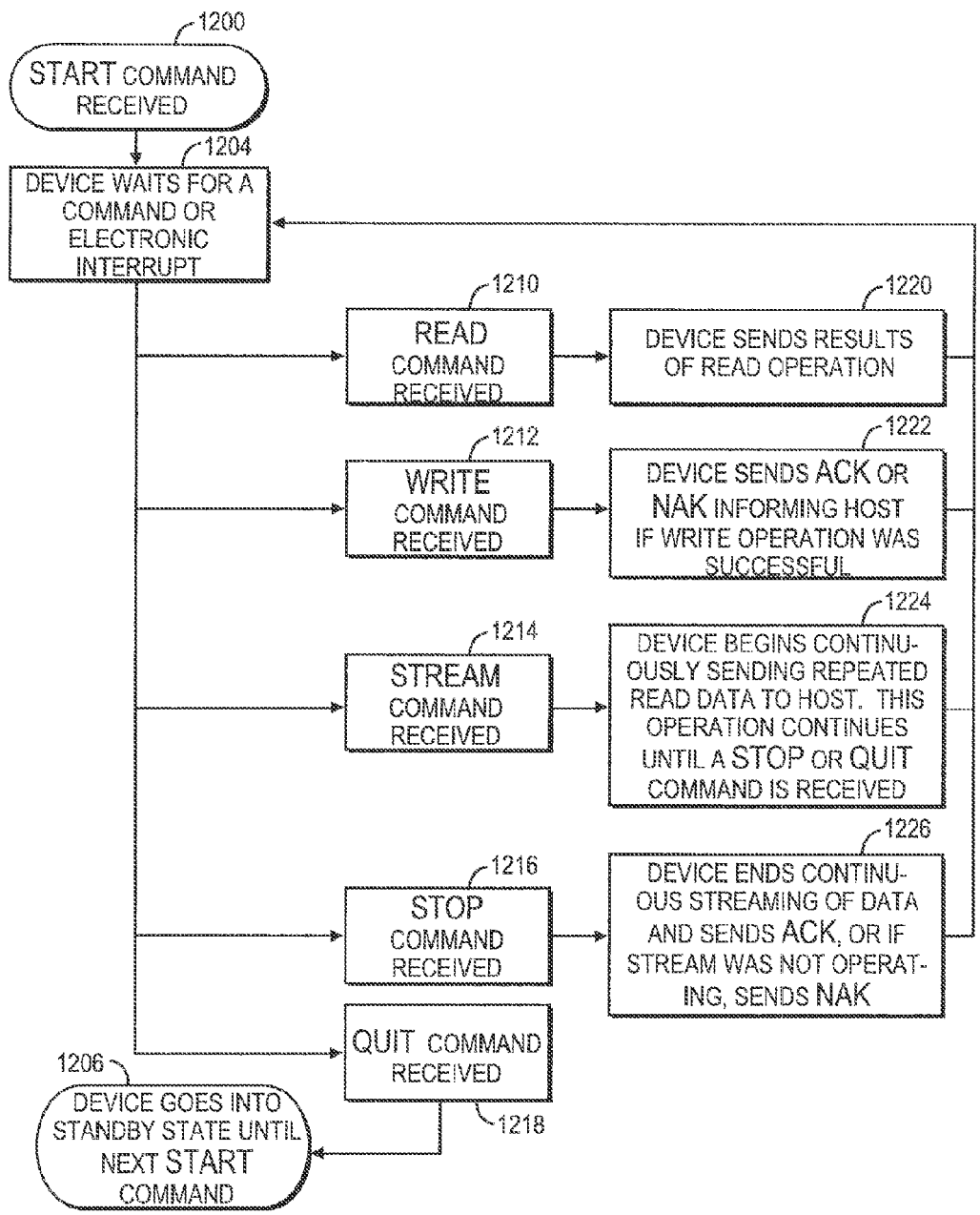
FIG. 12 is a flow chart summarizing the steps of Applicants' Integrated Device Data Flow Diagram.

Referring now to FIG. 12, when the system comes up the host addresses each of the test devices and moves any necessary calibration or configuration data to the host. As a general matter, this data is loaded before the test begins since this data is peculiar to each individual device even if they are of the same type. The evaluator selects a routine and the protocol for the test from the host display. Applicants' software verifies that the device is connected. A start command is then sent to the device requesting data to be sent to the host. The host sends audio and/or visual messages to the individual to start the test. As the test is being performed, additional messages are being sent to the individual as defined by the protocol.

When the individual completes the test he/she releases the test device and the individual is given an audio and/or visual instruction indicating the test is complete. The data the host has accumulated is then converted to pounds, kilograms or any other unit of measure and is analyzed according to the test protocol. If the test includes determining, for example, a maximum force number, then the host searches the data and stores that maximum number. If the device can do the sorting for maximum, and the test protocol only requires the maximum, the maximum number may be the only data sent to the host.

All tests are defined by a protocol. To perform timed tests, such as a fingering and handling test where pins are moved from one location to another and touch pads are touched, the device reports every time there is a sensed change in one of the sensors or touch pads. The activity is monitored by the host and is timed. For static strength devices, a start command is sent to the device and the device sends a continuous stream of force data to the host. The host monitors the data stream as defined by the protocol and determines when the test is complete. The device is turned off at the end of a test as defined by the protocol. The host looks for signals from the device as an individual is moving, placing, turning, gripping, touching, pressing or lifting depending on the test. It also verifies that a force is maintained for a period of time or that a specific weight is being lifted if that is part of the protocol.

Necessary time intervals can be programmed in advance by the evaluator. At the end of a test, the host sends a command to stop sending data and the device is turned off. Some test devices have the capability to power down on command, others automatically power off when data transmission stops. After the test is complete, the host analyzes the data, calculates averages and performs statistical analyses including standard deviations, coefficient of variation and other statistical analogies as defined by the protocol. The data is then saved in a database and/or report file and can be examined by the evaluator to develop a profile of the capacities of an individual. This can be used for example, to determine where an individual needs therapy, when an individual can go back to work, or an individual meets specific work standards.

Because Applicants' test devices comprise virtual devices, Applicants' system can have multiple tests running at the same time with one host. The evaluator selects a test mode for multiple tests on the host computer display panel and then selects the tests. Instructions to the individuals are handled through the use of audio commands instead of visual commands. If visual commands are needed for a test, an additional computer display panel is used. The interaction between the host and individual being tested occurs in the same manner as described above except it is issuing commands to individuals in parallel.

Applicants' apparatus is also capable of running tests in succession. Using prior art methods, a single test is set up and an individual is monitored to determine how well he or she performs the test. Using Applicants' apparatus and method a series of tests can be set wherein an individual moves from one test to other tests over a period of time. The series of tests can include a combination of any tests from intricate tests such as a finger dexterity test through a gross carrying and lifting test performed in succession.

Such a series of tests is valuable from a work hardening or conditioning standpoint. The evaluator shows the individual the tests to be performed prior to the testing. Assuming the protocol for the individual tests have been defined, a second protocol sends audio and/or visual instructions prompting the individual to move to the next test after completing a test. The whole sequence of tests is monitored by the host for completeness, performance and speed, during the tests and between tests.

Using Applicants' apparatus and method, multiple tests can be performed simultaneously, and independently, using a multitasking operating system. Applicants' method utilizes a multi-process threading model to keep simultaneous tests from interfering with one another. Applicants' multi-tasking is also used when performing multiple tests remotely across the internet from a single host.

As those skilled in the art will appreciate, Applicants' system is not limited to the test devices shown in FIGS. 1a and 1b. Additional test devices can be added and any of the above devices can be removed from the system. In addition, Applicants' system also allows for intermixing of integrated test devices and non-integrated devices.

Non-integrated devices use interfaces such as a non-integrated load cell wired to a Data Acquisition Interface built-in or external to a computer. For example, if a user wished to use the non-integrated standard JAMAR type electronic grip device typically used in physical and occupational therapy, he/she would add an electronic interface commonly available for such devices. The user would then add the compatible electronic plug and program the calibration details of the device into the host for use. Once this is done, the device is used and recognized whenever it is connected to the system.

Also, users can generate their own protocols using Applicants' apparatus, modify existing protocols, and/or add their own integrated test devices and generate their own protocols. For example, if a integrated device that measures dexterity operated by a "PIC" or other microcontroller were connected to the system, the features of the device could be programmed into the system once known. Then, each time the device is connected to the host, it would be recognized and controlled. These test devices, and how they function in a work capacities system, are well known in the industry today. Communication to most non-integrated devices is handled on a serial interface.

Another work capacity component available in the system is computerized work through a Hardening/Conditioning Protocol. Hardening/Conditioning is usually done to improve an individual's fitness in a specific area. Traditionally, isometric tests are used in an assessment protocol, but never in work hardening because of the risk that the individual may exceed safe physical limits; however, this system includes this capability. An isometric test is a non-motion test where the individual is pushing, pulling or lifting against a non-moving object that is attached to load cells or strain gages. The application has traditionally been directed toward sports therapy where an individual is trying to build functional strength. Routinely, the individual lifts, pushes or pulls with half target strength and then lifts, pushes or pulls with at a higher or full target strength alternately multiple times to build up muscle strength. This concept is programmed into a computerized measurable protocol. Using the lift test as an example, the individual sees a visual Symbol on the computer display at a base position. As he applies force, the Symbol moves toward a half lift Target Symbol Line on the display proportionally to the change in force. When the half target lift is reached, the Symbol touches the line, the first portion of the test, the half test, is complete. More strength is needed for the full lift so the Target Symbol Line moves farther from the base position. The greater the force the individual applies the further the Symbol moves. For the full target lift portion of the test, the Target Symbol Line is farther from the Symbol thereby symbolizing the required higher force. The system has a safety mechanism built into the software that notifies the individual if the individual applies a force higher than a percentage of the programmed values for the half and full test, and can shut down the system when necessary to reduce risk of injury of the individual. Variations on the test protocol include maintaining a force for a certain amount of time before proceeding to the next step in the test.

Applicants' apparatus and method also allows the evaluator to enter key job criteria and based upon these criteria, automatically generate a test protocol which is used to test the worker. For example, if it is known that the job for which the individual is being tested requires grip strength, lift strength, carrying, and forward work posture at specific quantifiers and/or work frequency levels, these criteria can be listed on the host program for automatic test protocol generation. TABLE 1 correlates Job Physical Demands with, inter alia, a Test Activity, a Protocol Routine, and a Performance Target.

TABLE 1

| Job Standard | | Automatic Test Protocol | | |
| --- | --- | --- | --- | --- |
| Job Physical Demand | Quantifier and/or Frequency | Test Activity | Protocol Routine | Performance Target |
| Grip-Right Hand | 110 lbs/Occasional | Grip-Right Hand | 4 Repetitions | 110 lb Avg. |
| Grip-Left Hand | 110 lbs/Occasional | Grip-Left Hand | 4 Repetitions | 110 lb Avg. |
| Lift-Bench Height | 80 lbs/Occasional | Static Lift | 4 Repetitions | 80 lb Avg. |
| | | Dynamic Lift | 4 Repetitions | 80 lb Avg. |
| Carrying | 80 lbs/Occasional | Carrying 80 lbs | 40 Foot Carry | 80% MTM Avg. |
| Reach-Forward | Frequent | Touch Panel-Forward | 400 Touch Cycles | 80% MTM Avg. |

In certain embodiments of Applicants' method, the host computer uses such lookup tables to generate a test protocol for a job function for which the individual is being tested. Once the test protocol is created, the host loads the routines into the individual's file to initiate the corresponding test routines. The evaluator always has the ability to edit the automatic test routines for issues related to safety, customer standards or other custom requirements.

Applicants' system 100 can be packaged in several standard shipping sized containers. Commonly used test hardware is packaged together with the host computer. This minimizes the number of containers to be transported when tests are needed at off site locations. The packaging is designed to allow transport of any combination of test devices required by the user.

Prior art systems utilize one or more solid posts or panels which exceed dimensional and weight limits for standard ground shipment or air shipment. In contrast, Applicants' apparatus includes a central post or monopole that can be disassembled into portable components. In the applicants system, the monopole can be used to mount test devices such as the Dynamic Strength Lift and Carrying Device, the Strength Push Pull and Lift Device and the Whole Body Coordination Device, and other hardware such as the controlling computer. This central post includes a T-Slot track, and allows other devices to be attached to it. This central post includes a shuttle which moves up or down thus allowing tests to be given at different positions.

Figure 7:
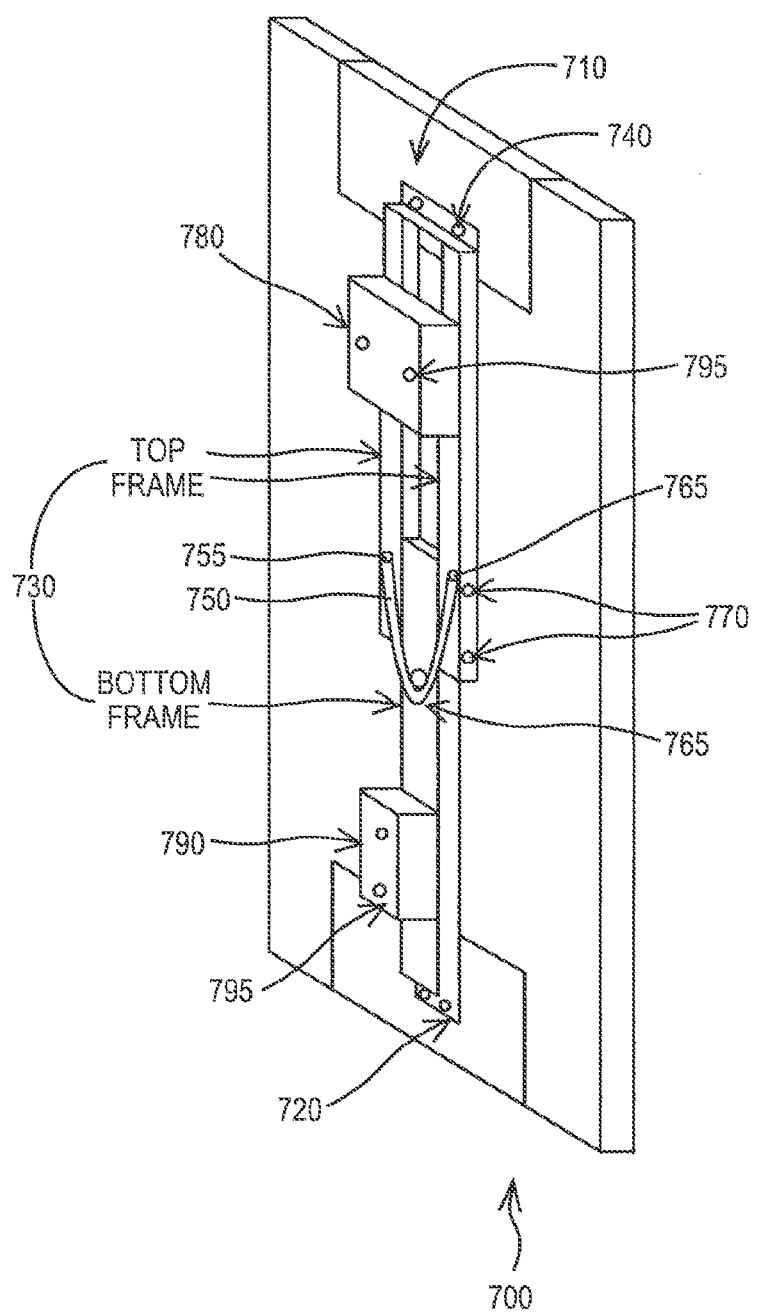
FIG. 7 is a perspective view of Applicants' portable Door Hanger System.

Applicants' system also comprises a compact and lightweight mechanical structure which allows the system to be hung on a door, thereby further enhancing the portability of Applicants' apparatus and method. Applicants' Work Capacities Testing System 700 is a portable assessment tool that is transportable and easily assembled using simple hand tools. This feature allows it to be used in any room having a door. As shown in FIG. 7, system 700 can be attached to a door using the top door hook 710, bottom door hook 720, and door frame rail 730.

Hanging the top and bottom door hooks to the door begins the assembly of the frame. Next, the door frame rail 730 is releaseably attached to top door hook 710 and bottom door hook 720 by inserting the end fasteners onto threaded studs and affixing those using thumbnuts 740. Next, the door frame rail is drawn tight to provide a rigid platform to attach the monopole.

A rope 750 having a ratchet tension connected to points 765 and 755 and over pivot point 760 is then used to draw the top and bottom parts of the door frame rail tight. When the desired tension is acquired, the frame adjustment bolts 770 are tightened to hold the door frame rail in place on the door. Door frame spacers 780 and 790 are attached at the top and bottom of the door frame rail using attachment bolts 795, as part of the door frame rail.

The door hanger hardware is now in place, and ready to have the monopole attached. As shown in FIG. 8, the monopole 810 and shuttle 820 are placed vertically and matched to the assembled door hanger hardware. On the back of the monopole are two attachment hangers 830 and 840 that are adjustable vertically to fit onto the two door frame spacers using attachment bolts 850. The attachment hangers are connected to the door frame spacers using a ball release pins 890 and 895. Finally, an optional floor 860 can be slid in place to connect at the bottom of the pole into the pivot hinge 870 and is attached using a ball release pin 880.

In other embodiments, Applicants' monopole system can be wall mounted using two or more fasteners. Referring now to FIGS. 21 and 22, each wall fastener comprises a pair of 90 degree angle assemblies 2210 and 2215. Portion 2230 of assembly 2210 is attached to portion 2260 of assembly 2215. Portion 2240 is attached to the wall and portion 2270 is attached to monopole 2130. Floor platform 2160 comprises two brackets 2150. Monopole 2130 is formed to include an aperture in the lower end. Crossbolt 2140 is disposed through a first bracket 2150, through the aperture in monopole 2130, and through the second bracket 2150, thereby releaseably fixturing floor platform 2160 to monopole 2130.

While the preferred embodiments of the present invention have been illustrated in detail, it should be apparent that modifications and adaptations to those embodiments may occur to one skilled in the art without departing from the scope of the present invention as set forth in the following claims.

We claim:

1. A handling/proprioception device for use in a work capacities testing apparatus, comprising:
    a first panel;
    a pin;
    a first light emitter disposed on said first panel, wherein said first light emitter is capable of being selectively illuminated, wherein said first panel is formed to include a first aperture adjacent said first light emitter, and wherein said pin can be removeably inserted into said first aperture;
    a second light emitter disposed on said first panel, wherein said second light emitter is capable of being selectively illuminated, wherein said first panel is formed to include a second aperture adjacent said second light emitter, and wherein said pin can be removeably inserted into said second aperture;
    a third light emitter disposed on said first panel, wherein said third light emitter is capable of being selectively illuminated, wherein said first panel is formed to include a third aperture adjacent said third light emitter, and wherein said pin can be removeably inserted into said third aperture; and
    a fourth light emitter disposed on said first panel, wherein said fourth light emitter is capable of being selectively illuminated, wherein said panel is formed to include a fourth aperture adjacent said fourth light emitter, and wherein said pin can be removeably inserted into said fourth aperture.

2. The handling/proprioception device of claim 1, wherein said handling/proprioception device further comprises a faceted object comprising a plurality of faces, wherein each of said plurality of faces comprises different visually observable information, wherein said handling/proprioception device is formed to include a fifth aperture dimensioned to receive a cube.

3. The handling/proprioception device of claim 2, further comprising a finger flexion device comprising a second panel; a finger touch pad light disposed on said second panel, wherein said finger touch pad light can be selectively illuminated; a finger touch pad disposed on said second panel adjacent said finger touch pad light; a first palm rest location disposed on said second panel adjacent said finger touch pad; and a second palm rest location disposed on said second panel adjacent said finger touch pad.

4. The handling/proprioception device of claim 3, further comprising:
    a data acquisition system comprising a USB interface;
    a first voltage regulator;
    a second voltage regulator;
    a third voltage regulator;
    a decoder interconnected with said data acquisition system, said first voltage regulator, said second voltage regulator, and said third voltage regulator, wherein said decoder selectively activates one or more voltage regulators;
    faceted object sensors and LED circuitry interconnected with said first voltage regulator, wherein said faceted object sensors and LED circuitry is capable of determining the orientation of said cube;
    pin sensor circuitry interconnected with said second voltage regulator, wherein said PIN sensors and LED circuitry is capable of sensing pin placement;
    handling touch pad circuitry interconnected with said second voltage regulator, wherein said handling touch pad circuitry is capable of determining when a user touches said second panel; and
    finger touch pad and touch pad circuitry interconnected with said third voltage regulator, wherein said finger touch pad and touch pad circuitry is capable of determining when a user touches said first panel.

\* \* \* \* \*